(12) United States Patent
Korkuch

(10) Patent No.: US 11,697,002 B2
(45) Date of Patent: *Jul. 11, 2023

(54) EXPANDABLE INTRODUCER SHEATH FOR MEDICAL DEVICE

(71) Applicant: ABIOMED, Inc., Danvers, MA (US)

(72) Inventor: Christopher Nason Korkuch, Beverly, MA (US)

(73) Assignee: ABIOMED, INC., Danvers, MA (US)

( * ) Notice: Subject to any disclaimer, the term of this patent is extended or adjusted under 35 U.S.C. 154(b) by 299 days.

This patent is subject to a terminal disclaimer.

(21) Appl. No.: 17/192,560

(22) Filed: Mar. 4, 2021

(65) Prior Publication Data

US 2021/0260344 A1 Aug. 26, 2021

Related U.S. Application Data

(63) Continuation of application No. 15/917,042, filed on Mar. 9, 2018, now Pat. No. 10,967,152.
(Continued)

(51) Int. Cl.
*A61M 25/06* (2006.01)
*A61M 25/00* (2006.01)

(52) U.S. Cl.
CPC ...... *A61M 25/0662* (2013.01); *A61M 25/005* (2013.01); *A61M 25/0023* (2013.01);
(Continued)

(58) Field of Classification Search
CPC .......... A61M 25/0662; A61M 25/0023; A61M 25/005; A61M 2025/0024;
(Continued)

(56) References Cited

U.S. PATENT DOCUMENTS 4,699,611 A 10/1987 Bowden
5,139,486 A 8/1992 Moss
(Continued)

FOREIGN PATENT DOCUMENTS

EP 2676641 A2 12/2013
EP 2995268 A1 3/2016
(Continued)

OTHER PUBLICATIONS

Office Action issued in Korean Patent Application No. 10-2019-7029641, dated Nov. 22, 2022, 18 pages.
(Continued)

*Primary Examiner* — Kelly J Bekker
*Assistant Examiner* — Mohammed S Adam
(74) *Attorney, Agent, or Firm* — Botos Churchill IP Law LLP

(57) ABSTRACT

An expandable medical sheath can include a sheath body having a lumen that extends between proximal and distal ends of the sheath. The sheath can have first and second members where the first member has a different elastic modulus than the second member such that one provides elasticity to the sheath and the other provides column strength. The first and second members can be coupled together in alternating sections to form the tubular sheath or the stiffer members can be embedded in the elastic member along all or a portion of the longitudinal length of the sheath. The sheath can automatically move to an expanded state to allow a larger diameter medical device to pass through the lumen, and once through the sheath can automatically return to its initial diameter.

20 Claims, 17 Drawing Sheets

Related U.S. Application Data

(60) Provisional application No. 62/470,026, filed on Mar. 10, 2017.

(52) U.S. Cl.
CPC ............... *A61M 2025/0024* (2013.01); *A61M 2025/0025* (2013.01); *A61M 2025/0675* (2013.01); *A61M 2025/0681* (2013.01); *A61M 2025/0687* (2013.01)

(58) Field of Classification Search
CPC .. A61M 2025/0675; A61M 2025/0681; A61M 2025/0687
See application file for complete search history.

(56) References Cited

U.S. PATENT DOCUMENTS

| | | |
|---|---|---|
| 5,234,425 A | 8/1993 | Fogarty et al. |
| 5,304,142 A | 4/1994 | Liebl et al. |
| 5,320,611 A | 6/1994 | Bonutti et al. |
| 5,395,341 A | 3/1995 | Slater |
| 5,397,310 A | 3/1995 | Chu et al. |
| 5,407,430 A | 4/1995 | Peters |
| 5,488,960 A | 2/1996 | Toner |
| 5,492,530 A | 2/1996 | Fischell et al. |
| 5,536,255 A | 7/1996 | Moss |
| 5,573,517 A | 11/1996 | Bonutti et al. |
| 5,653,697 A | 8/1997 | Quiachon et al. |
| 5,911,702 A | 6/1999 | Romley et al. |
| 5,935,122 A | 8/1999 | Fourkas et al. |
| 5,944,691 A | 8/1999 | Querns et al. |
| 5,971,993 A | 10/1999 | Hussein et al. |
| 6,120,480 A | 9/2000 | Zhang et al. |
| 6,197,016 B1 | 3/2001 | Fourkas et al. |
| 6,338,730 B1 | 1/2002 | Bonutti et al. |
| 6,428,556 B1 | 8/2002 | Chin |
| 6,458,867 B1 | 10/2002 | Wang et al. |
| 6,579,264 B1 | 6/2003 | Rossi |
| 6,613,038 B2 | 9/2003 | Bonutti et al. |
| 6,692,462 B2 | 2/2004 | Mackenzie et al. |
| 6,814,715 B2 | 11/2004 | Bonutti et al. |
| 6,989,003 B2 | 1/2006 | Wing et al. |
| 7,025,746 B2 | 4/2006 | Tal |
| 7,722,567 B2 | 5/2010 | Tal |
| 7,727,251 B2 | 6/2010 | Spurchise et al. |
| 7,927,309 B2 | 4/2011 | Palm |
| 8,475,431 B2 | 7/2013 | Howat |
| 8,597,277 B2 | 12/2013 | Lenker et al. |
| 8,663,541 B2 | 3/2014 | Chun et al. |
| 8,672,888 B2 | 3/2014 | Tal |
| 8,758,402 B2 | 6/2014 | Jenson et al. |
| 8,814,832 B1 | 8/2014 | Al-Rashdan et al. |
| 9,126,015 B2 | 9/2015 | Krolik et al. |
| 9,320,508 B2 | 4/2016 | Carroux |
| 9,446,218 B2 | 9/2016 | Accisano |
| 9,474,884 B1 | 10/2016 | Aman et al. |
| 9,586,033 B2 | 3/2017 | Tegels |
| 9,693,800 B2 | 7/2017 | Aman et al. |
| 9,895,245 B2 | 2/2018 | Puckett et al. |
| 9,974,561 B2 | 5/2018 | Benning et al. |
| 10,143,491 B2 | 12/2018 | Clancy et al. |
| 10,449,071 B2 | 10/2019 | Jordan |
| 10,499,895 B2 | 12/2019 | Anderson |
| 10,537,718 B2 | 1/2020 | Lederman et al. |
| 10,625,050 B2 | 4/2020 | McFarland |
| 10,682,157 B2 | 6/2020 | Bierman et al. |
| 10,874,511 B2 | 12/2020 | Ginn |
| 2002/0072712 A1 | 6/2002 | Nool et al. |
| 2003/0014068 A1 | 1/2003 | Bonutti et al. |
| 2004/0087968 A1 | 5/2004 | Core |
| 2005/0149105 A1 | 7/2005 | Leeflang et al. |
| 2006/0041270 A1 | 2/2006 | Lenker et al. |
| 2006/0135981 A1 | 6/2006 | Lenker et al. |
| 2006/0287574 A1 | 12/2006 | Chin |
| 2006/0287669 A1 | 12/2006 | Casey et al. |
| 2008/0046005 A1 | 2/2008 | Lenker et al. |
| 2008/0051734 A1 | 2/2008 | Bonutti et al. |
| 2008/0051821 A1 | 2/2008 | Gephart |
| 2008/0082165 A1 | 4/2008 | Wilson et al. |
| 2008/0183136 A1 | 7/2008 | Lenker et al. |
| 2009/0240202 A1 | 9/2009 | Drasler et al. |
| 2010/0198160 A1 | 8/2010 | Voss |
| 2011/0144690 A1 | 6/2011 | Bishop et al. |
| 2011/0152763 A1 | 6/2011 | Bishop et al. |
| 2011/0166637 A1 | 7/2011 | Irwin et al. |
| 2012/0109056 A1 | 5/2012 | Rasmussen |
| 2012/0130192 A1 | 5/2012 | Rasmussen et al. |
| 2013/0131718 A1 | 5/2013 | Jenson et al. |
| 2013/0131787 A1 | 5/2013 | Ginn |
| 2013/0138201 A1 | 5/2013 | Ginn |
| 2013/0184736 A1 | 7/2013 | Aman et al. |
| 2013/0317438 A1 | 11/2013 | Ellingwood et al. |
| 2013/0317481 A1 | 11/2013 | Ellingwood et al. |
| 2013/0338677 A1 | 12/2013 | Schwitzer et al. |
| 2014/0275795 A1 | 9/2014 | Little et al. |
| 2014/0336752 A1 | 11/2014 | Ginn et al. |
| 2015/0094795 A1 | 4/2015 | Ginn et al. |
| 2016/0066948 A1 | 3/2016 | Ellingwood et al. |
| 2016/0067454 A1 | 3/2016 | Furnish et al. |
| 2016/0128723 A1 | 5/2016 | Ginn et al. |
| 2016/0213882 A1 | 7/2016 | Fitterer et al. |
| 2016/0220358 A1 | 8/2016 | Wilson et al. |
| 2016/0338828 A1 | 11/2016 | Ginn |
| 2016/0354583 A1 | 12/2016 | Ellingwood et al. |
| 2017/0000973 A1 | 1/2017 | Otake et al. |
| 2017/0014232 A1 | 1/2017 | Ginn et al. |
| 2017/0056063 A1 | 3/2017 | Ellingwood et al. |
| 2017/0080180 A1 | 3/2017 | Eilat |
| 2017/0095640 A1 | 4/2017 | Rogers et al. |
| 2017/0265891 A1 | 9/2017 | Mcfarland |
| 2017/0281908 A1 | 10/2017 | Ellingwood et al. |
| 2018/0071091 A9 | 3/2018 | Ginn et al. |
| 2018/0256859 A1 | 9/2018 | Korkuch |
| 2018/0271558 A1 | 9/2018 | Bierman et al. |
| 2019/0030294 A1 | 1/2019 | McLaughlin et al. |
| 2019/0070394 A1 | 3/2019 | Appling et al. |
| 2019/0183525 A9 | 6/2019 | Ginn et al. |
| 2019/0247617 A1 | 8/2019 | Farnan |
| 2019/0247627 A1 | 8/2019 | Korkuch et al. |
| 2019/0307589 A1 | 10/2019 | Goldberg et al. |
| 2020/0360140 A1 | 11/2020 | Ginn et al. |
| 2020/0360165 A1 | 11/2020 | Ginn et al. |
| 2020/0367929 A1 | 11/2020 | Ginn et al. |

FOREIGN PATENT DOCUMENTS

| | | |
|---|---|---|
| JP | 2008011867 A | 1/2008 |
| JP | 5199434 B2 | 2/2013 |
| JP | 2016189839 A | 11/2016 |
| JP | 2019076330 A | 5/2019 |
| WO | 2004037333 A1 | 5/2004 |
| WO | 2019008922 A1 | 1/2019 |

OTHER PUBLICATIONS

International Search Report and Written Opinion PCT/US2018/021695, dated Jun. 22, 2018 (9 pages).
IPRP / Written Opinion in International Application No. PCT/US2018/021695, dated Sep. 10, 2019 (Sep. 10, 2019), 6 pages.
Office Action from corresponding Indian Patent Application No. 201917039226 dated Jan. 28, 2022 (5 pages).
Office Action from corresponding Japanese Patent Application No. 2019-548906 dated Dec. 1, 2021 (9 pages).
Examination Report issued in corresponding Australian Patent Application No. 2018230449 dated Oct. 26, 2022 (4 pp. ).

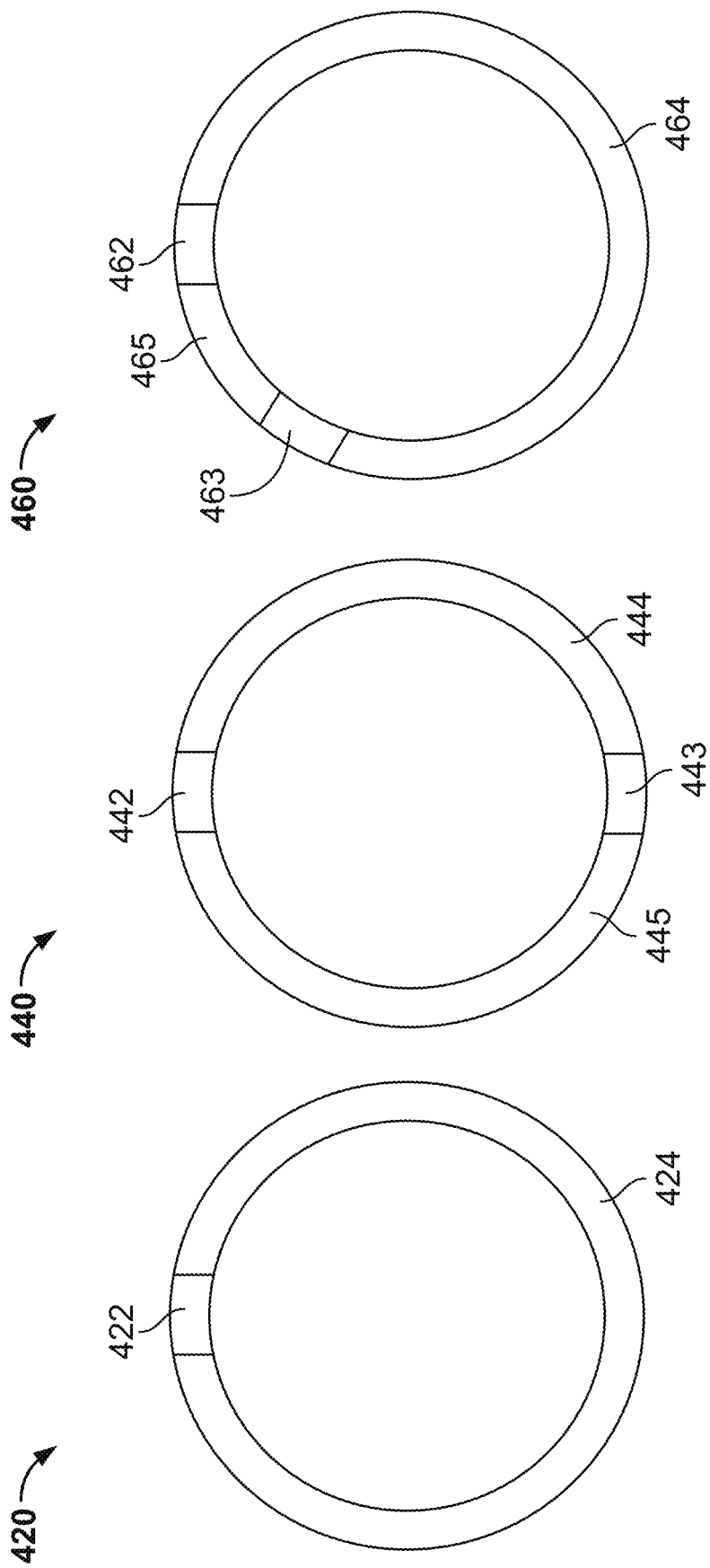

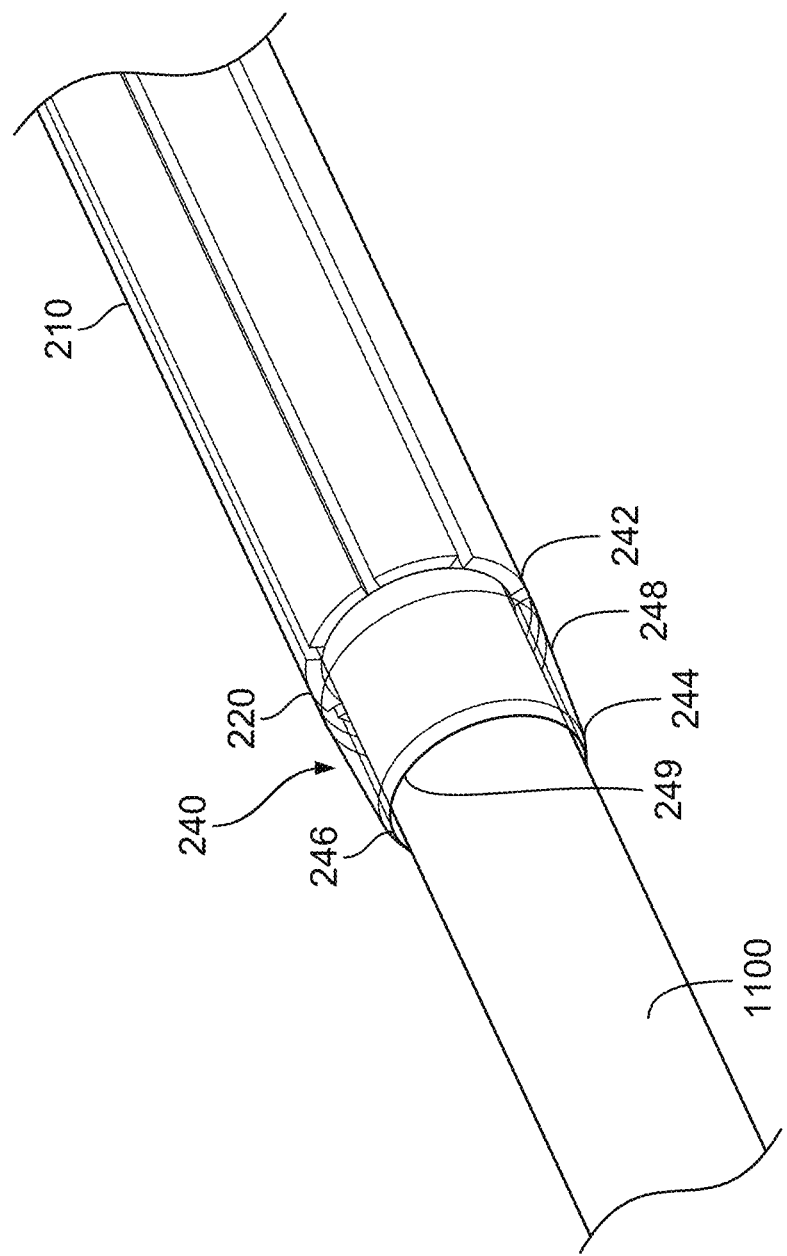

EXPANDABLE INTRODUCER SHEATH FOR MEDICAL DEVICE

CROSS-REFERENCE TO RELATED APPLICATIONS

This application is a continuation of U.S. patent application Ser. No. 15/917,042, filed Mar. 9, 2018, which application claims priority to U.S. provisional application No. 62/470,026, filed Mar. 10, 2017, the content of each of which is hereby incorporated by reference herein in its entirety.

BACKGROUND OF THE INVENTION

A medical device, such as an intracardiac heart pump assembly, can be introduced into a patient in various ways. In general, a heart pump can be introduced in the heart to pump blood from the heart into a vessel to support the function of the heart. When deployed in the heart, a heart pump assembly pulls blood from the left ventricle of the heart and expels blood into the aorta, or pulls blood from the inferior vena cava (IVC), bypasses the right atrium and right ventricle, and expels blood into the pulmonary artery. Heart pump assemblies are introduced surgically or percutaneously during a cardiac procedure through the vascular system. In one common approach, pump assemblies are inserted by a catheterization procedure through the femoral artery using a sheath, such as a peel-away introducer sheath. The sheath can alternatively be inserted in other locations such as in the femoral vein or any path for delivery of a pump for supporting either the left or right side of the heart.

The peel-away introducer sheath can be inserted into the femoral artery through an arteriotomy to create an insertion path for the pump assembly. A portion of the pump assembly is then advanced through an inner lumen of the introducer and into the artery. Once the pump assembly has been inserted, the peel-away introducer sheath is peeled away. A repositioning sheath can then be advanced over the pump assembly and into the arteriotomy. Replacing the introducer sheath and the repositioning sheath during insertion of a medical device can prevent blood clot formation which would otherwise occur in the introducer sheath, and prevent or reduce bleeding at the insertion site in the skin and/or at the insertion site within the vessel because of better fixation of the sheath to the patient when used with a hemostatic valve.

Since peel-away introducer sheaths are not radially expandable, the inner diameter of the peel-away introducer sheath must always be large enough to accommodate the passage of the largest diameter portion of the pump assembly such as the pump head even if other parts of the pump assembly, such as the catheter, have a significantly smaller diameter. This means that once the pump is inserted, the peel-away introducer creates an opening that has an outer diameter that is wider than necessary to allow passage of the pump catheter into the vessel. Accordingly, the peel-away introducer sheath is peeled away and replaced with a lower-profile repositioning sheath. But peeling away the introducer has several disadvantages. For example, peel-away introducers can peel too easily and risk being torn prematurely, leading to bleeding or vascular complications. On the other hand, peel-away introducers may require excessive force to peel away. If a physician applies too much force, when the introducer finally gives, the physician may inadvertently shift the position of the pump within the heart. Having to peel away the introducer also complicates the design of the hemostatic valve located in the hub of the introducer which also needs to separate. Additionally, the peel away action is an added step that the user must be aware of and trained on, and which requires added time to perform. Further, the need for a repositioning sheath to guide and/or reposition the pump within the heart adds complexities to the intravascular procedure due to the above-described multi-step nature of insertion of a repositioning sheath.

Further, if a peel-away introducer sheath is required, there is also a larger arteriotomy opening to close after the system is removed. The larger size of the peel away sheath can be intimidating to some users and carries a negative perception that may limit adoption. To have a close fit to the delivery catheter body and to minimize the cross-section of the repositioning sheath through most of the indwelling length during longer term dwell, the inner diameter of the repositioning sheath is smaller than the peel away sheath. This prevents removal of the pump without also removing the repositioning sheath which loses access to the vessel and requiring the immediate attention to closing the access site upon system/sheath removal.

Some medical introducers for applications other than inserting heart pumps have expandable sheath bodies which may expand radially to allow passage of percutaneous devices into the patient's vasculature. These introducers are inserted having inner diameters smaller than the outer diameter of the device being introduced. The introducers expand to allow passage of the device through the sheath and into the vasculature and then shrink again after the device has passed. In the current state, these expandable introducers are for relatively short term use and are stand-alone components. Since the current expandable sheaths are intended for short term use, they are not configured for preventing thrombosis between the sheath body and an indwelling catheter. Additionally, some current expandable sheaths are completely flexible and therefore do not provide any rigidity within their structure thereby requiring the use of a repositioning sheath during insertion of a percutaneous medical device. Furthermore, the current expandable sheaths do not include means for sealing the arteriotomy for long durations or for preventing migration of the inserted device (in and out of the vessel).

SUMMARY OF INVENTION

Systems, devices and methods for insertion of a medical device (e.g., intravascular medical device) are presented. The devices are delivered through an expandable introducer sheath. Use of an introducer sheath capable of expansion allows a smaller puncture size to be used for insertion and can allow the vessel to more easily recoil to a smaller diameter after insertion of the pump. Additionally, because the medical device only momentarily passes through the vessel wall, the opening in the vessel is expected to be smaller than if a larger non-expandable sheath is used. Still further, since the medical device only momentarily passes through the vessel, if friction between the device, sheath, and vessel wall is minimized, there is a reduced axial load and reduced stress on the vessel. That is, the sheath is a smaller size and is not pushing or pulling the vessel along the axis of the insertion/removal path and instead, when the device passes through the vessel, the vessel is expanded outward radially. The expandable introducer sheath is configured to remain in an insertion path (e.g., an arteriotomy) for relatively long durations (e.g., >1 hr, >2 hr, >6 hr, or any suitable duration).

Since the expandable introducer sheath need not be removed, the risk of premature peel-away is essentially eliminated and the risk of shifting the introduced device inadvertently (e.g., by overuse of force during peel-away) is reduced or eliminated. Furthermore, allowing the expandable introducer sheath to remain in an insertion path simplifies the use of the introduced device by reducing the number of steps in the insertion procedure, namely by eliminating the peel-away process.

In a first aspect, an expandable medical sheath includes a sheath body having an inner surface and an outer surface, the inner surface defining a lumen that extends between proximal and distal ends of the sheath. The medical sheath also includes first and second members, each disposed between the inner and outer surfaces of the sheath and each extending between the proximal and distal ends of the sheath, the first member comprising a first material and the second member comprising a second material. The sheath is expandable from an unexpanded state to an expanded state to allow the passage of a portion of a medical device through the lumen, the portion of the medical device having a transverse cross-sectional area larger than a transverse cross-sectional area of the lumen when the sheath is in the unexpanded state.

The non-homogeneous structure of the sheath body allows for the sheath to expand to the expanded state during the passage of the medical device in the lumen of the sheath body, and return to the unexpanded state once the medical device leaves the lumen of the sheath body. This momentary expansion of the sheath body minimizes the size of the arteriotomy required when inserting the sheath into the vasculature of the patient. This also minimizes damage to a vessel wall as a smaller opening would be required to accommodate the sheath body in the unexpanded state, thereby minimizing thrombotic occlusion of the vessel. A smaller opening also minimizes the time to reach hemostasis after removal of the medical device.

Such an expandable sheath also does away with the need for the conventional set up of having multiple sheaths, such as a peel-away introducer sheath and a repositioning sheath for the introduction of a medical device (e.g. a percutaneous heart pump) into the arteriotomy. Such an expandable sheath also allows a repositioning sheath to be used in conjunction with it, if necessary. Once the expandable sheath is positioned in an arteriotomy, it maintains access to a vessel even after the medical device is removed, should such access be required for other medical procedures. This increases procedural efficiency of any medical procedure as there is no need to peel away the introducer sheath for the insertion of a repositioning sheath each time access to the arteriotomy is required. Furthermore, more accurate repositioning of the medical device can be achieved with the expandable introducer sheath as the expandable introducer sheath is fixed in position once inserted whereas the insertion of a separate repositioning sheath does involve multiple steps where chances of misplacing the medical device are significantly higher.

The expandable sheath therefore removes the need for an introducer sheath and a repositioning sheath during any medical procedure requiring access to an arteriotomy of a patient. Infection can thus be minimized as an introducer sheath (after being peeled away) will not be resting outside the patient after insertion of a repositioning sheath during a medical procedure. The effective consolidation of the introducer sheath and the repositioning sheath into a single device can decrease the costs involved during a medical procedure. Further, since only a single sheath is required to gain arteriotomic access to a vessel, less bleeding may be involved during long term use of a percutaneous medical device such as a heart pump.

According to a first implementation of the present disclosure, there is provided an expandable medical sheath comprising a sheath body having an inner surface and an outer surface, the inner surface defining a lumen that extends between proximal and distal ends of the sheath. The expandable sheath also comprises first and second members, each disposed between the inner and outer surfaces of the sheath and each extending between the proximal and distal ends of the sheath, the first member comprising a first material and the second member comprising a second material. Here the sheath is expandable from an unexpanded state to an expanded state to allow the passage of a portion of a medical device through the lumen, the portion of the medical device having a transverse cross-sectional area larger than a transverse cross-sectional area of the lumen when the sheath is in the unexpanded state.

In some implementations, the first material has a higher elastic modulus than the second material. In other implementations, the first material comprises at least one of: polyether ether ketone (PEEK), a polyether block amide (such as PEBAX), a polyethylene material, a high-density polyethylene (HDPE) material, a medium-density polyethylene (HDPE) material, a low-density polyethylene (LDPE) material, a crack-resistant material, a material with a low coefficient of friction, and a material with an elastic modulus of about 40 ksi. In certain implementations the second material comprises at least one of: ethylene-vinyl acetate (EVA), styrene-butadiene copolymer (SBC), synthetic rubber, an elastomer, an elastic material, a material with an elastic modulus of about 1.6 ksi, and a material with a yield strain in excess of 200%. In other implementations, the sheath automatically returns to the unexpanded state after passage of the portion of the medical device.

In certain implementations, the expandable sheath also comprises a plurality of first members and a plurality of second members, the plurality of first members being equal to in number to the plurality of second members. In some implementations, the first and second members are arranged symmetrically in alternating sections about a longitudinal axis of the sheath. In other implementations, the first and second members are arranged non-symmetrically in alternating sections about a longitudinal axis of the sheath. In some implementations, the second material encapsulates alternating sections of the first material. According to certain implementations, a diameter of the outer surface at the proximal end of the sheath is larger than a diameter of the outer surface at the distal end of the sheath, when the sheath is in the unexpanded state. In some implementations, the sheath is radially expandable, while the length of the sheath remains substantially unchanged when the sheath expands.

In some implementations, the expandable sheath comprises a hub coupled to the proximal end of the sheath, the hub having at least one hemostatic valve in communication with the lumen of the sheath. In other implementations, the inner surface has an irregular geometry to minimize contact between the sheath body and the medical device. In certain implementations, the inner surface comprises at least one rib extending between proximal and distal ends of the sheath. In other implementations, the expandable sheath comprises a tip attached to the distal end of the expandable sheath. In some implementations, the tip comprises at least one of: ethylene-vinyl acetate (EVA), styrene-butadiene copolymer (SBC), synthetic rubber, an elastomer, an elastic material, a material with an elastic modulus of about 1.6 ksi, and a material with a yield strain in excess of 200%.

In certain implementations, the tip comprises an inner surface defining a tip lumen that extends between proximal and distal ends of the tip, the tip lumen being in fluid communication with the lumen of the expandable sheath. In other implementations, an outer diameter of the proximal end of the tip is larger than an outer diameter of the distal end of the tip such that the tip is tapered. In further implementations, a diameter of the inner surface at the proximal end of the tip is larger than a diameter of the inner surface at the distal end of the tip. In certain implementations, the tip comprises the second material. In other implementations, the first material is substantially stiffer than the second material, and the second material is substantially more elastic than the first material. In certain implementations, the length of the sheath remains substantially unchanged when the sheath expands from the unexpanded state to the expanded state.

According to a further implementation of the present disclosure, there is provided an expandable medical sheath comprising a sheath body having an inner surface and an outer surface, the inner surface defining a lumen that extends between proximal and distal ends of the sheath. The expandable sheath further comprises a plurality of first members and a plurality of second members, each disposed between the inner and outer surfaces of the sheath, each first member comprising a first material and each second member comprising a second material, and each of the first and second members being alternately arranged around the lumen. Here the sheath is expandable from an unexpanded state to an expanded state to allow the passage of a portion of a medical device through the lumen, the portion of the medical device having a transverse cross-sectional area larger than a transverse cross-sectional area of the lumen when the sheath is in the unexpanded state.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 4A shows a transverse cross section of the illustrative expandable sheath of FIG. 2 with a flexible member and a rigid member;

FIG. 4B shows a transverse cross section of the illustrative expandable sheath of FIG. 2 with two flexible members and two rigid members arranged in a symmetric manner;

FIG. 4C shows a transverse cross section of the illustrative expandable sheath of FIG. 2 with two flexible members and two rigid members arranged in a non-symmetric manner;

FIG. 11 shows an isometric view of a distal end of the illustrative expandable sheath of FIG. 2 assembled with a dilator during insertion of the expandable sheath;

DETAILED DESCRIPTION

Figure 1:
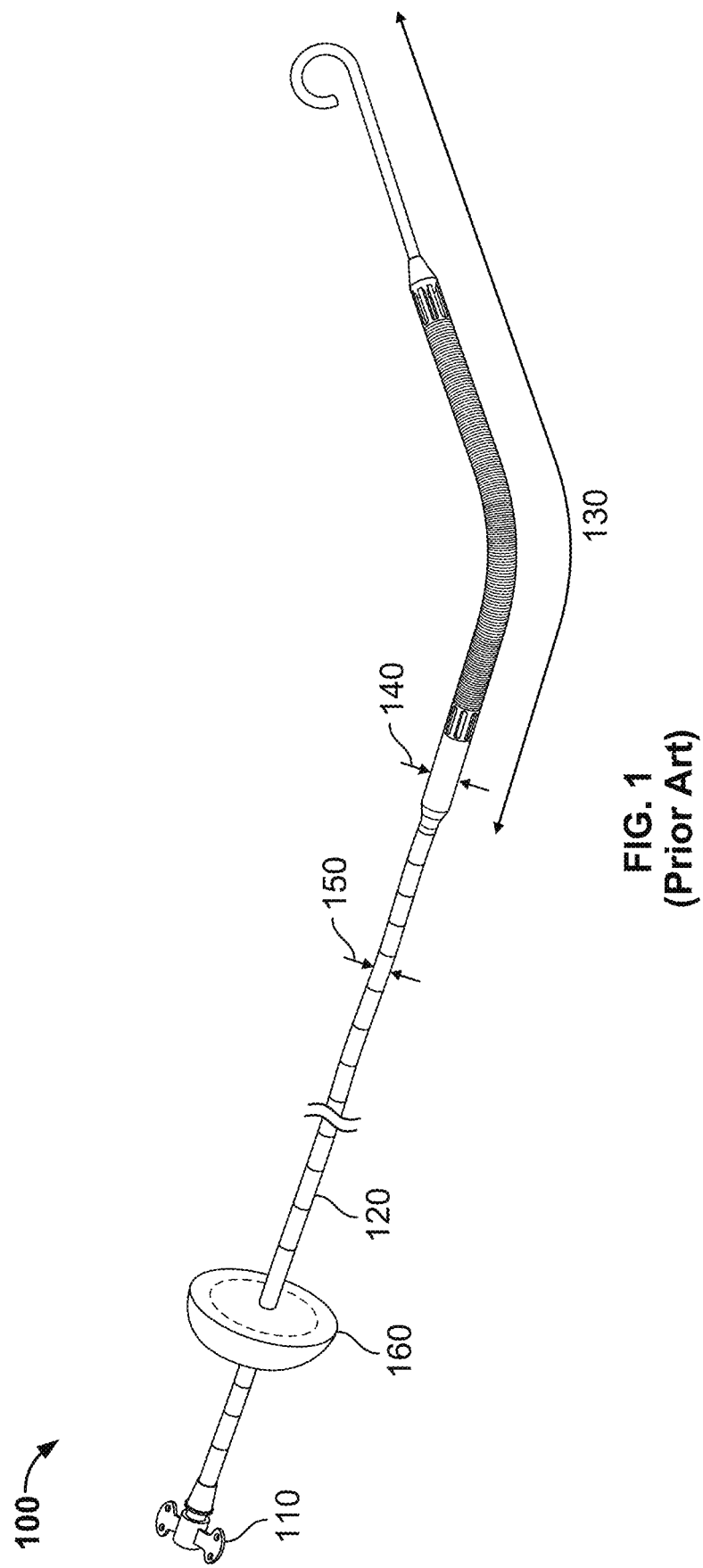
FIG. 1 shows an isometric view of an illustrative prior art medical device.

To provide an overall understanding of the systems, method, and devices described herein, certain illustrative embodiments will be described. Although the embodiments and features described herein are specifically described for use in connection with a percutaneous heart pump system, it will be understood that all the components and other features outlined below may be combined with one another in any suitable manner and may be adapted and applied to other types of medical devices such as TAVR delivery systems, cardiac therapy and cardiac assist devices, including balloon pumps, cardiac assist devices implanted using a surgical incision, and the like.

The systems, methods and devices described herein provide an expandable sheath assembly for the insertion of a medical device (e.g., a percutaneous heart pump) into a blood vessel through a vessel aperture. The expandable medical sheath comprises a sheath body having an inner surface and an outer surface, the inner surface defining a lumen that extends between proximal and distal ends of the sheath. The medical sheath also includes first and second members, each disposed between the inner and outer surfaces of the sheath and each extending between the proximal and distal ends of the sheath, the first member comprising a first material and the second member comprising a second material. The sheath is expandable from an unexpanded state to an expanded state to allow the passage of a portion of a medical device through the lumen, the portion of the medical device having a transverse cross-sectional area larger than a transverse cross-sectional area of the lumen when the sheath is in the unexpanded state.

The non-homogeneous structure of the sheath body allows for the sheath to expand to the expanded state during the passage of the medical device in the lumen of the sheath body, and return to the unexpanded state once the medical device leaves the lumen of the sheath body. This momentary expansion of the sheath body minimizes the size of the arteriotomy required when inserting the sheath into the vasculature of the patient. This also minimizes damage to a vessel wall as a smaller opening would be required to accommodate the sheath body in the unexpanded state, thereby minimizing thrombotic occlusion of the vessel. A smaller opening also minimizes the time to reach hemostasis after removal of the medical device. Such an expandable sheath does away with the need for the conventional set up of having multiple sheaths, such as a peel-away introducer sheath and a repositioning sheath for the introduction of a medical device (e.g. a percutaneous heart pump) into the arteriotomy. Such an expandable sheath also allows such a conventional set up to be used in conjunction with it, if necessary. Once the expandable sheath is positioned in an arteriotomy, it maintains access to a vessel even after the medical device is removed, should such access be required for other medical procedures. This increases procedural efficiency of any medical procedure as there is no need to re-gain alternative access or re-insert a second introducer in the same access site.

In certain embodiments, the expandable sheath is compressed to a compressed state during insertion into the vasculature of the patient. Once inserted, the expandable sheath expands to a resting configuration. The resting configuration of the sheath body allows for the sheath to expand to an expanded state during the passage of the medical device in the lumen of the sheath body, and return to the resting configuration once the medical device leaves the lumen of the sheath body. The compressed state of the sheath body also minimizes the size of the arteriotomy required when inserting the sheath into the vasculature of the patient. This also minimizes damage to a vessel wall as a smaller opening would be required to accommodate the sheath body in the unexpanded state, thereby minimizing thrombotic occlusion of the vessel. A smaller opening also minimizes the time to reach hemostasis after removal of the medical device.

The expandable sheath therefore removes the need for an introducer sheath and a repositioning sheath during any medical procedure requiring access to an arteriotomy of a patient. Infection will thus be minimized as a repositioning sheath will not be resting outside the patient prior to the removal of the peel away sheath during a medical procedure. The effective consolidation of the introducer sheath and the repositioning sheath into a single device undoubtedly decreases the costs involved during a medical procedure. Further, since only a since sheath is required to gain arteriotomic access to a vessel, less bleeding would be involved during long term use of a percutaneous medical device such as a heart pump.

FIG. 1 shows an illustrative mechanical assist device (MAD) such as a percutaneous pump 100 according to certain implementations. The pump 100 comprises a pump handle 110, a pump head 130, a catheter 120 connecting the pump handle 110 to the pump head 130, and a connecting hub 160. The catheter 120 is tubular and has a substantially uniform outer diameter. The catheter 120 enables the pump head 130 and the pump handle 110 to be in electro-mechanical communication. The pump handle 110 is in communication with control circuitry which allows the control of the pump head 130. The pump head 130 contains electro-mechanical components that enable the device to perform various tasks within the body of a patient, such as pump blood from a location within the body. The pump head 130 has a diameter 140 that is larger than the diameter 150 of the catheter 120. An example of such a percutaneous pump is the Impella 2.5™ system (Abiomed, Inc., Danvers, Mass.). It will be understood that while a percutaneous heart pump is described herein, any other percutaneous medical device can be used in conjunction with the present disclosure.

Figure 2:
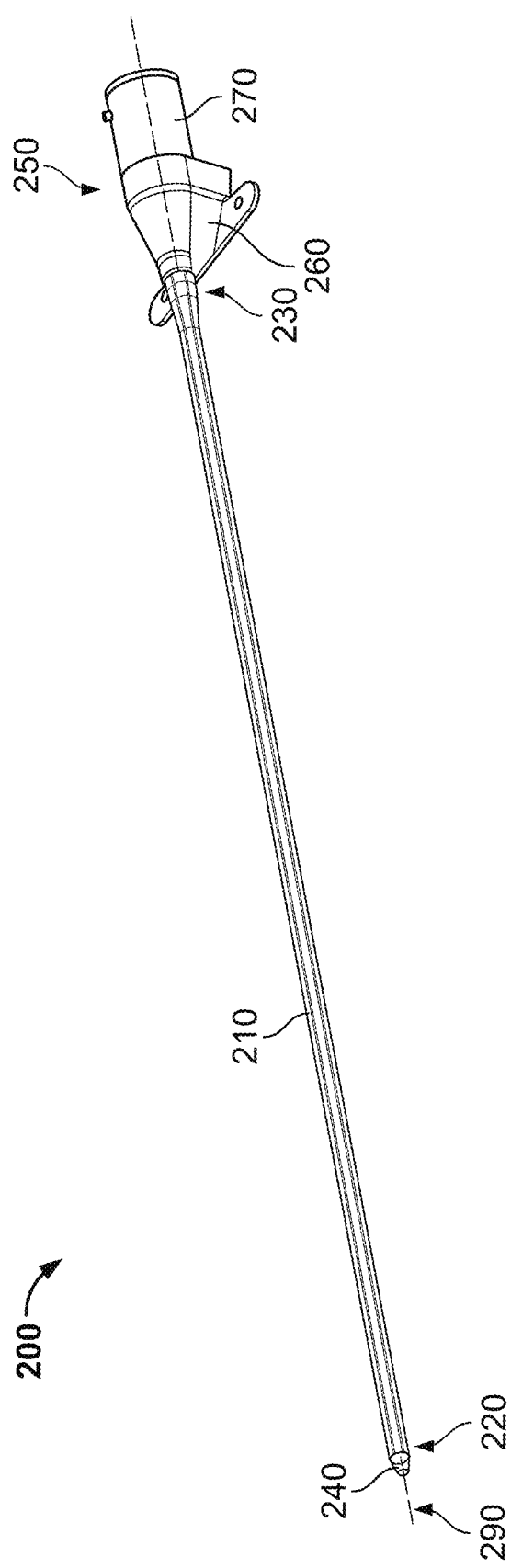
FIG. 2 shows an isometric view of an illustrative expandable sheath.

FIG. 2 shows an illustrative expandable sheath 200 according to certain implementations. The expandable sheath 200 comprises a sheath body 210 having a distal end 220 and a proximal end 230. A flexible tip 240 having an internal lumen is attached to the distal end 220 of the sheath body 210. A hub assembly 250 is coupled to the proximal end 230 of the sheath body 210. The hub assembly 250 comprises a flexible portion 260 and a rigid portion 270. The flexible portion 260 couples the proximal end 230 of the sheath body 210 to the distal end of the rigid portion 270 of the hub assembly 250. The sheath body 210 has a longitudinal axis 290. In certain implementations, the sheath body 210 is tubular.

Figure 3A:
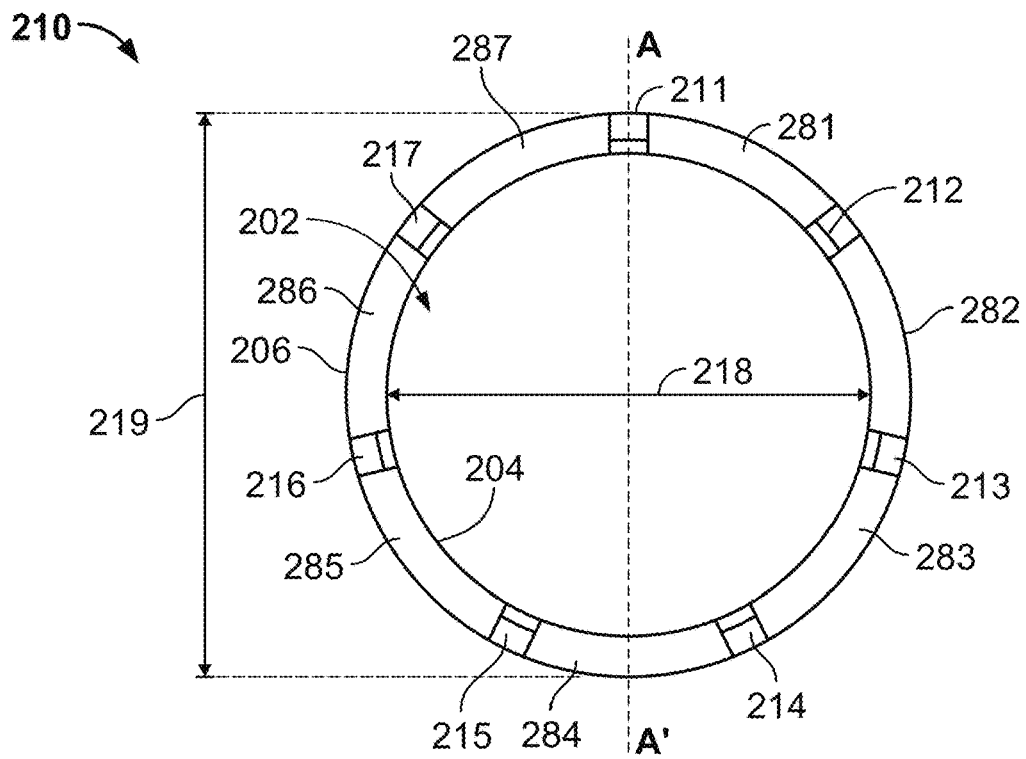
FIG. 3A shows a transverse cross section of the illustrative expandable sheath of FIG. 2 in an unexpanded state.

FIG. 3A shows a transverse cross-section of the sheath body 210. The sheath body 210 has an inner surface 204 and an outer surface 206. The inner surface 204 defines a lumen 202 that extends between the proximal end 230 and the distal end 220 of the sheath body 210 for the momentary passage of a portion of a medical device, such as the percutaneous pump 100 of FIG. 1. The lumen 202 of the sheath body 210 has an internal diameter 218. The sheath body 210 has an outer diameter 219. The sheath body 210 is non-homogenous. The sheath body 210 comprises flexible sections 211-217 and rigid sections 281-287. The flexible sections 211-217 provide a means of expansion of the internal diameter 218 of the sheath body 210 and return to its unexpanded state thereby allowing the passage of a medical device having a larger diameter than the inner diameter 218 of the sheath 200. The rigid sections 281-287 are substantially stiffer than the flexible sections 211-217. The rigid sections 281-287 provide column strength and stiffness for axial compressive loading. Such axial loading occurs during insertion of a medical device 100 into the expandable sheath 200. The rigid sections 281-287 therefore resist buckling during axial insertion of the medical device 100 into the sheath 200. The flexible sections 211-217 and the rigid sections 281-287 are present in equal number. Each of the flexible 211-217 and rigid 281-287 sections extend along the length of the sheath from the proximal end 230 to the distal end 220. Additionally, each of the flexible 211-217 and rigid 281-287 sections are disposed between the inner surface 204 and the outer surface 206 of the sheath body 210. The flexible sections 211-217 and the rigid sections 281-287 are alternately arranged to form the sheath body 210 such that each flexible section 211-217 is adjacent to a rigid section 281-287, and, similarly, each rigid section 281-287 is adjacent to a flexible section 211-217. Alternative configurations of the expandable sheath will be detailed in the sections that follow and with reference to FIGS. 14A to 14C. Further, while a single lumen 202 has been described, it will be understood that multiple lumens may be present in the sheath body 210. Such multiple lumens are described in U.S. patent application Ser. No. 14/827,741, entitled "Dual Lumen Sheath for Arterial Access," the entire contents of which are hereby incorporated by reference. Multiple lumens facilitate the use of a stylet and/or a guide wire with the expandable sheath 200.

The flexible sections 211-217 comprise a flexible material. The flexible material is an elastic material with an elastic modulus of about 1.6 ksi. Ksi is a unit of pressure, representing thousands of pounds per square inch. In some implementations, the flexible material is a material with a yield strain of about 200%. In some implementations, the flexible material contains a radiopaque filler such as bismuth oxychloride or barium sulfate in concentrations of 5% to 40% by weight. In certain implementations, the flexible material comprises any one of: ethylene-vinyl acetate (EVA), styrene-butadiene copolymer (SBC), synthetic rubber, or any other elastomer. The rigid sections 281-287 comprise a rigid material. The rigid material is a polyethylene or polyurethane material with an elastic modulus of about 40 ksi. In some implementations the rigid material contains a radiopaque filler such as bismuth oxychloride or barium sulfate in concentrations of 5% to 40% by weight. In some implementations, the rigid material is any one of a high-density polyethylene (HDPE) material, a medium-density polyethylene (MDPE) material, a low-density polyethylene (LDPE) material, polyether ether ketone (PEEK), and a polyether block amide (such as PEBAX). In certain implementations, the rigid material is a crack-resistant material. In some implementations, the rigid material may also be a material with a low coefficient of friction.

In some implementations, the inner surface 204 of the sheath body 210 may have an irregular geometry to minimize contact with a medical device (e.g., medical device 100) that is advancing through the lumen 202. Such irregular geometry may include structures that span at least a portion of the longitudinal length of the sheath body 210. Such structures may include ribs, projections, indentations, for example, that reduce the amount of contact the inner surface 204 of the sheath body 210 makes with a medical device 100 that is advanced through the lumen 202. In one implementation, the inner surface 204 of the sheath body 210 may be provided with at least one rib or projection that runs along at least a portion of the longitudinal length of the sheath 210. Such structures may appear as raised features that protrude from the inner surface 204 of the sheath body 210. In other implementations, the inner surface 204 of the sheath body 210 may be provided with at least one indentation that runs along at least a portion of the longitudinal length of the sheath 210. Such structures may appear as recessed features that appear as depressions on the inner surface 204 of the sheath body 210. In further implementations, a combination of projections and indentations may be provided along at least a portion of the longitudinal length of the sheath body 210.

Figure 3B:
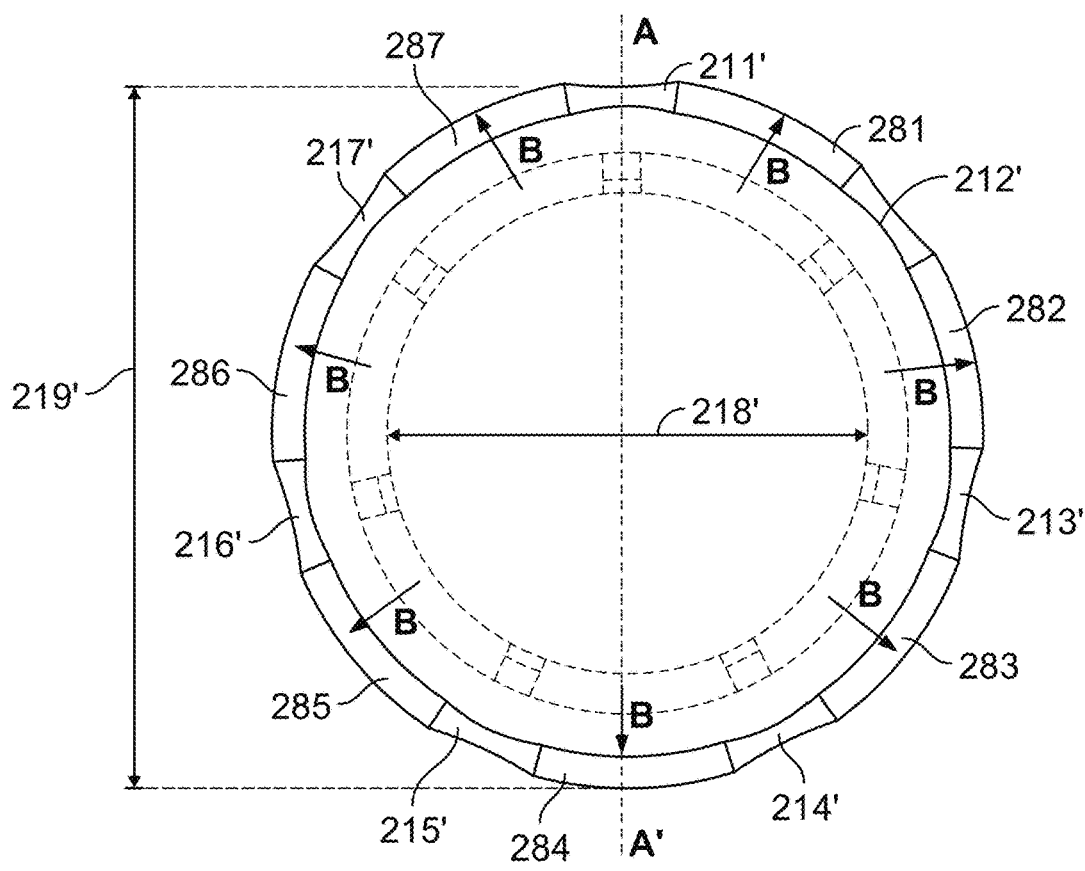
FIG. 3B shows a transverse cross section of the illustrative expandable sheath of FIG. 2 in an expanded state.

The arrangement of the flexible 211-217 and rigid 281-287 sections of the sheath body 210 enable the sheath 200 to radially expand about the longitudinal axis 290 when a portion of a medical device 100 that is larger than the transverse cross-sectional area of the lumen 202 when in an unexpanded state is introduced into the sheath body 210. Such radial expansion occurs when the largest diameter 140 of the medical device 100 is greater than the unexpanded diameter 218 of the lumen 202. It can also be said that such radial expansion occurs when the transverse cross-sectional area of the portion of the medical device 100 is larger than the transverse cross-sectional area of the lumen 202 when in an unexpanded state. Thus when the medical device 100 is inserted into the lumen 202 of the sheath 200, the lumen 202 expands and the diameter of the lumen 202 increases from 218 to 218' as shown in FIG. 3B. The external diameter 219 of the sheath body 210 increases from 219 to 219'. In this expanded state, the flexible sections 211-217 are forced to deform so as to accommodate the medical device 100 in the lumen 202. Such deformation is indicated by the radially outward arrows B in FIG. 3B. When the flexible sections 211-217 deform, they increase in width (see difference between section 211 and expanded section 211', for example), thereby causing the overall diameter 218 of the lumen 202 to increase to 218' as depicted in FIG. 3B. It naturally follows that when the diameter 218 of the lumen 202 increases to 218', the transverse cross-sectional area of the lumen 202 also increases. The increased transverse cross-sectional area of the lumen 202 enables the portion of medical device 100 that is larger than the transverse cross-sectional area of the lumen 202 when in an unexpanded state to move within the sheath body 210. FIG. 3B illustrates the deformation of the flexible sections 211-217 in FIG. 3A to sections 211'-217' in FIG. 3B. Such deformation of the flexible sections 211-217 is within elastic limit of the flexible material used for the flexible sections 211-217. These flexible sections 211-217 therefore do not permanently deform. Thus, after the portion of the medical device 100 that is larger than the transverse cross-sectional area of the lumen 202 when in an unexpanded state has passed through the sheath body 210, the deformed flexible portions 211'-217' automatically return to their unexpanded width as shown in FIG. 3A, and the expanded diameter 218' of the lumen 202 decreases to 218 as indicated in FIG. 3A. It will be understood that the sheath body 210 will return from the expanded state to the unexpanded state passively and with no intervention by using elastic strain developed in the flexible sections 211-217. It should also be noted that due to the alternate arrangement of the rigid sections 281-287 and the flexible sections 211-217, and their respective material compositions (i.e. that the rigid sections 281-287 comprise a material that is substantially stiffer than the material used for the flexible sections 211-217), the length of the sheath body 210 remains substantially unchanged when the sheath expands from the unexpanded state (with diameter 218) to the expanded state (with diameter 218').

In FIG. 3A, seven flexible sections 211-217 and seven rigid sections 281-287 are shown. However it will be understood that any number of flexible 211-217 and rigid 281-287 sections can be used in connection with the present disclosure. Additionally, these sections can be arranged in a symmetrical or non-symmetrical manner about the longitudinal axis 290 of the sheath body 210. For example, in certain implementations as shown in FIG. 4A, the sheath body 420 comprises one flexible section 422 and one rigid section 424. FIG. 4B illustrates another implementation in which the sheath body 440 comprises two flexible sections 442, 443 and two rigid sections 444, 445. In FIG. 4B, the flexible and rigid sections 442-445 are arranged in a symmetric manner about the longitudinal axis of the sheath body 440 (not shown). FIG. 4C illustrates an alternative non-symmetrical arrangement of flexible sections 462, 463 and rigid sections 464, 465 of the sheath body 460.

Figure 5:
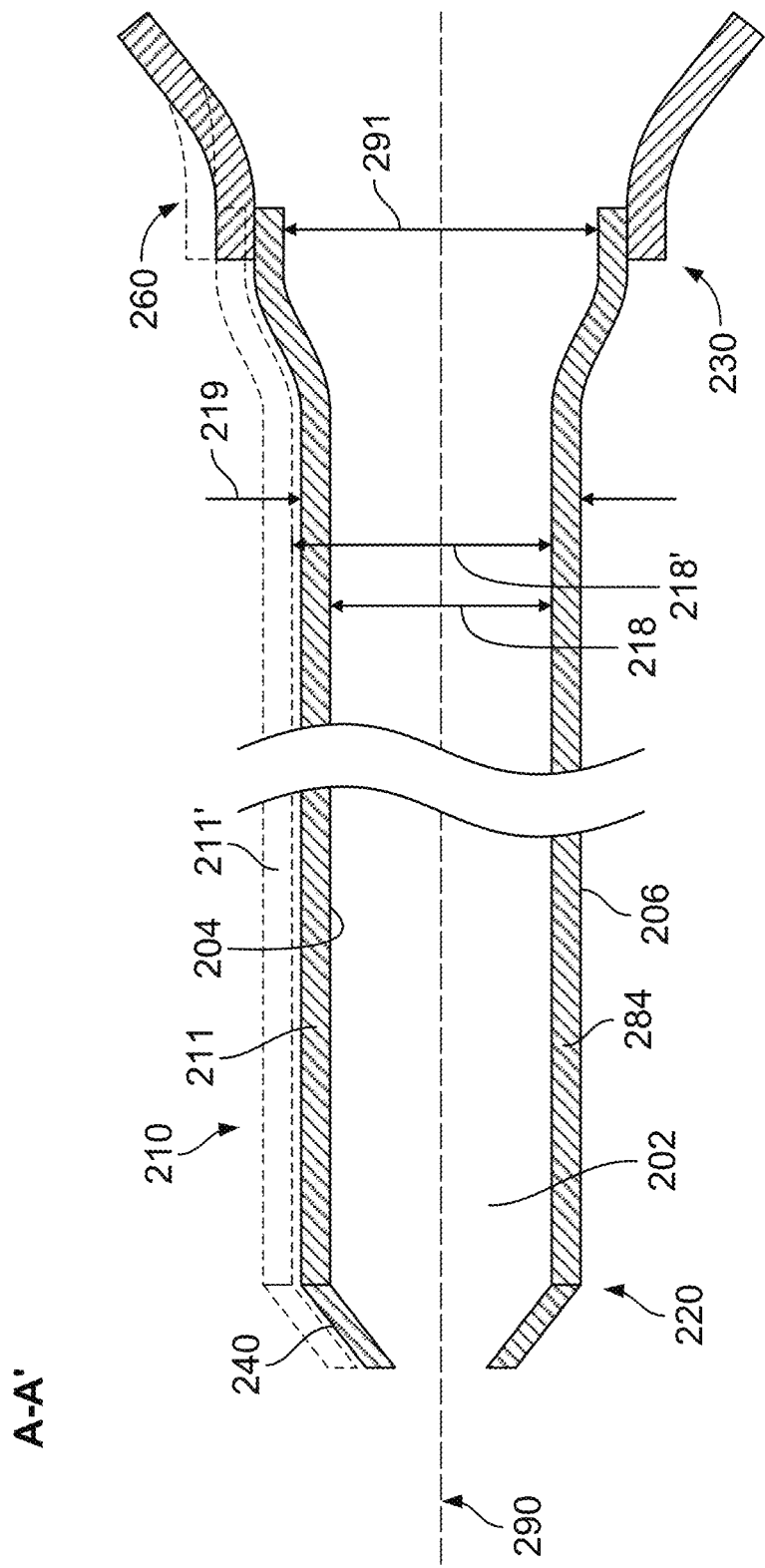
FIG. 5 shows a lateral cross section of an illustrative expandable sheath for arterial access for a medical device such as the device of FIG. 2.

FIG. 5 shows a lateral cross-sectional view of the sheath body 210 taken along the line A-A' as shown in FIGS. 3A and 3B. The figure shows flexible section 211 and rigid section 284 when the sheath body 210 is unexpanded (as shown in FIG. 3A). In the unexpanded state, the lumen 202 has an unexpanded diameter 218. When a portion of a medical device 100 is inserted into the sheath body 210, the flexible sections 211-217 deform thereby increasing the diameter of lumen 202 to 218'. In particular, flexible section 211 deforms to 211' while the rigid section does not substantially deform (as shown in FIG. 3B). The flexible tip 240 and the flexible portion 260 of the hub assembly 250 are also shown in FIG. 5, and will be discussed in the sections that follow.

Figure 6:
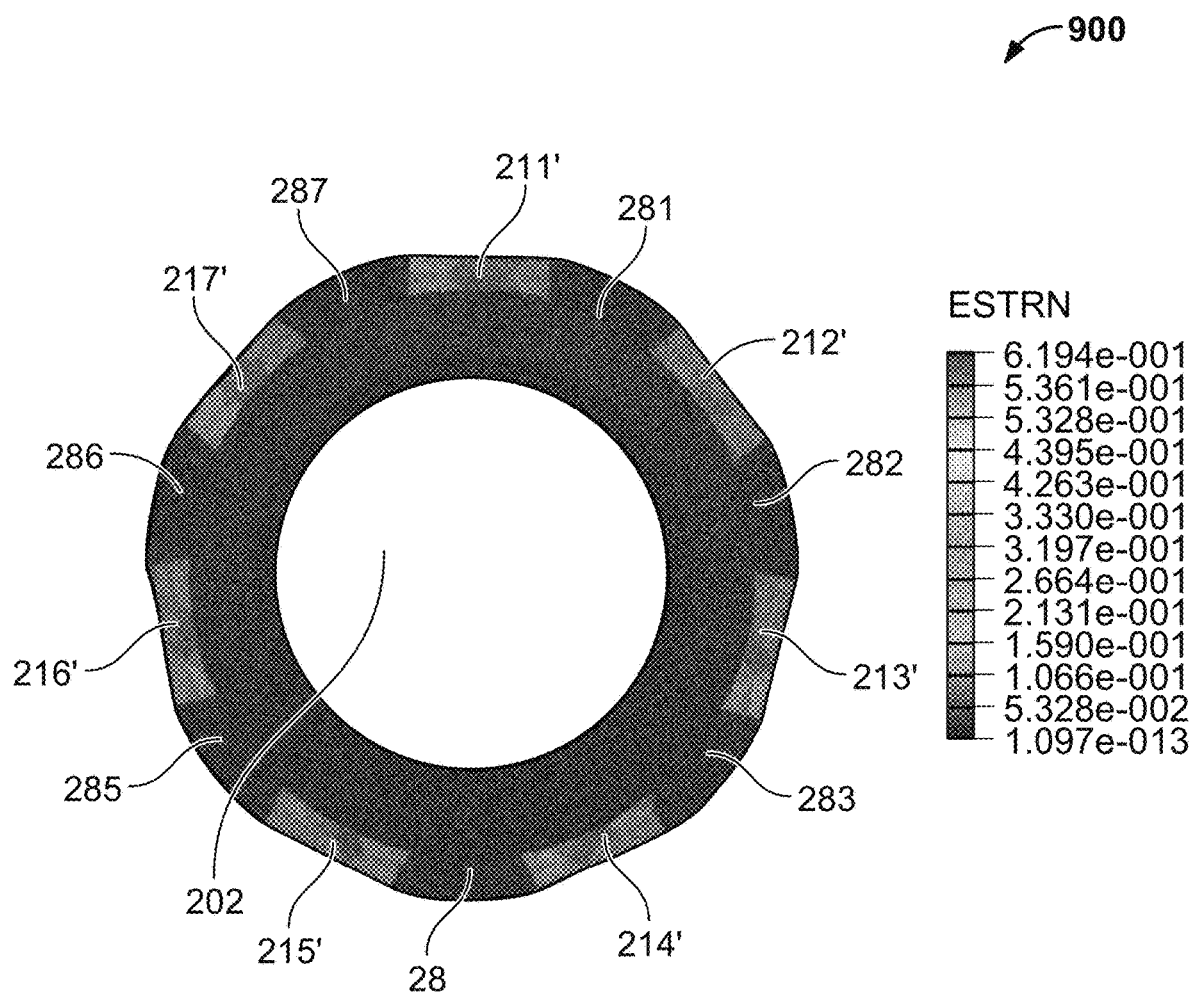
FIG. 6 shows a transverse cross section of the illustrative expandable sheath of FIG. 2 which indicates the anticipated strain during expansion of the sheath body.

FIG. 6 illustrates the anticipated strain along a transverse cross-sectional area of the sheath body 210 when the sheath body 210 is in the expanded state for the passage of the medical device 100 in the lumen 202 (as depicted in FIG. 3B). Rigid sections 281-287 show little to no strain (indicated by the darker shading), while deformed flexible sections 211'-217' show high levels of strain (indicated by the lighter shading).

Figure 7:
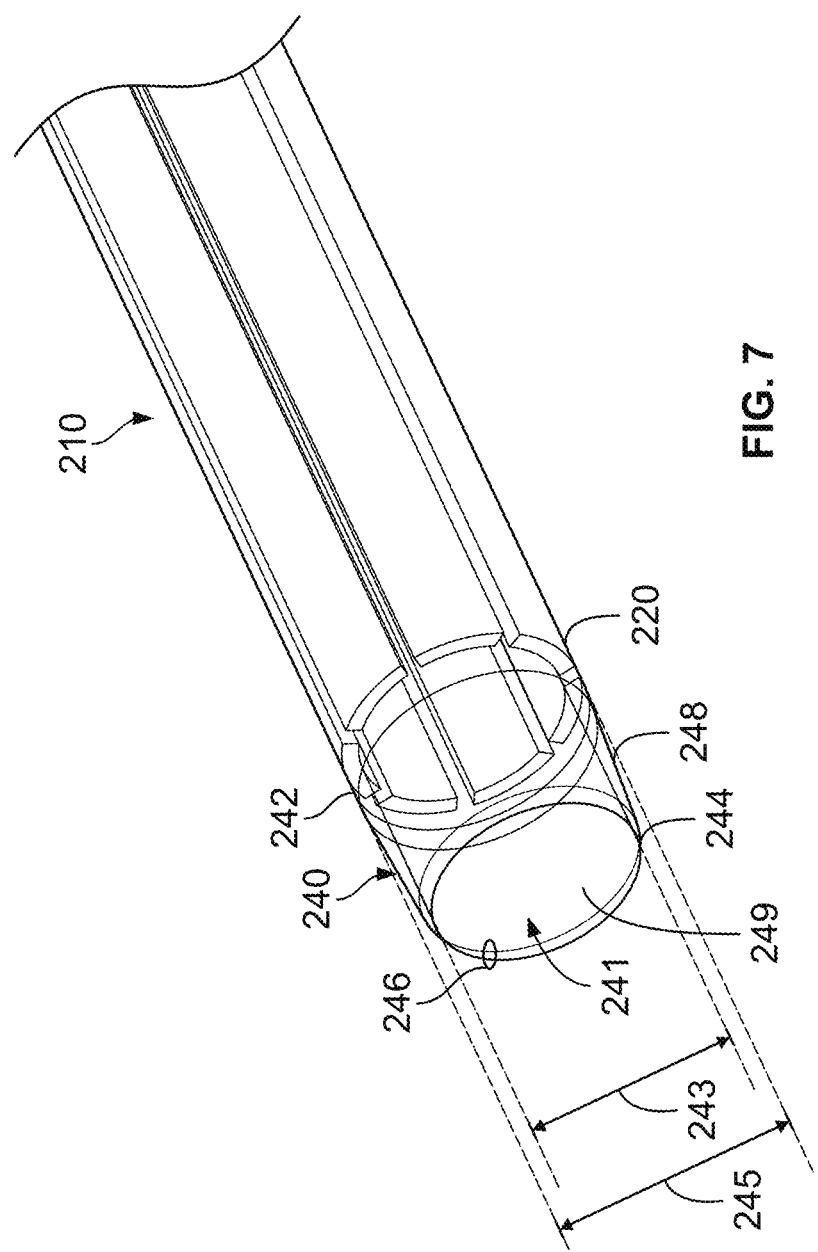
FIG. 7 shows an isometric view of a distal end of the illustrative expandable sheath of FIG. 2.

FIG. 7 shows a perspective view of the sheath body 210 which terminates with a flexible tip 240. The tip 240 comprises a proximal end 242, a distal end 244, an outer surface 248 and an inner surface 249. The inner surface 249 defines an opening 241 with an inner diameter 243, and the outer surface 248 has an outer diameter 245. The proximal end 242 of the tip 240 is coupled to the distal end 220 of the sheath body 210 such that the lumen 202 and the opening 241 of the tip 240 are seamlessly in communication with each other. This allows for easy passage of the medical device 100 as it leaves the sheath 200 and progresses into the vasculature of a patient. The inner surface 249 of the tip 240 is slightly tapered such that the inner diameter 243 is larger at the proximal end 242 than at the distal end 244 of the tip 240. This creates a slight inference fit with the smallest diameter on the medical device 100. This slight inference of the distal tip 240 with the medical device 100 helps seal any fluid or blood from entering the opening 241 and hence the lumen 202 while allowing the lumen 202 to be flushed with fluid. The outer surface 248 of the tip 240 is also tapered towards the distal end 244 such that the outer diameter 245 is larger at the proximal end 242 than at the distal end 244. The distal end 244 of the tip 240 terminates at a leading edge 246. The outer diameter of the leading edge 246 has a radius to facilitate smooth insertion of the sheath 200 into the vasculature of a patient. The tip 240 is highly resilient and will not exhibit permanent deformation (such as flaring or splitting). In certain implementations, the tip 240 comprises the same flexible material as the flexible sections 211-217 of the sheath body 210. Further, the tapered surfaces 248, 249 result in thinning of the walls of the tip 240 towards the distal end 244. This allows for less traumatic retrieval of an oversized medical device during removal from the vasculature of a patient. In certain implementations, the tip 240 comprises a flexible material. The flexible material is an elastic material with an elastic modulus of about 1.6 ksi. In some implementations, the flexible material is a material with a yield strain of about 200%. In certain implementations, the flexible material comprises ethylene-vinyl acetate (EVA). In further implementations, the flexible material comprises an elastomer. In other implementations, the flexible material may comprise a material similar to that used for the flexible sections 211-217 of the sheath body 210.

Figure 8:
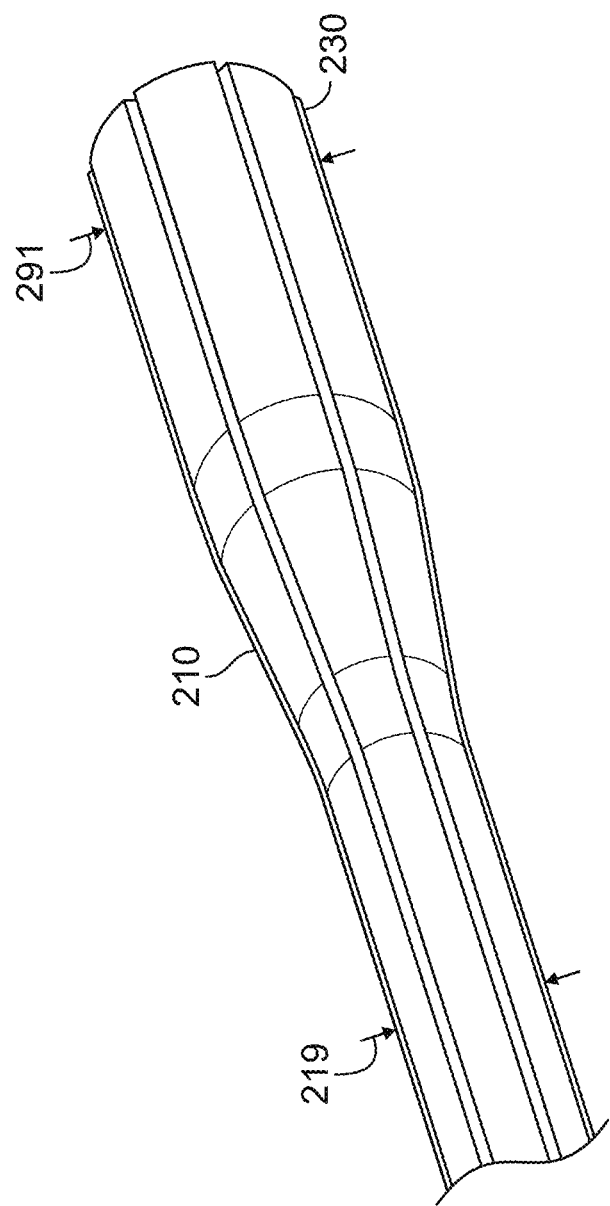
FIG. 8 shows an isometric view of a proximal end of the illustrative expandable sheath of FIG. 2.
Figure 9:
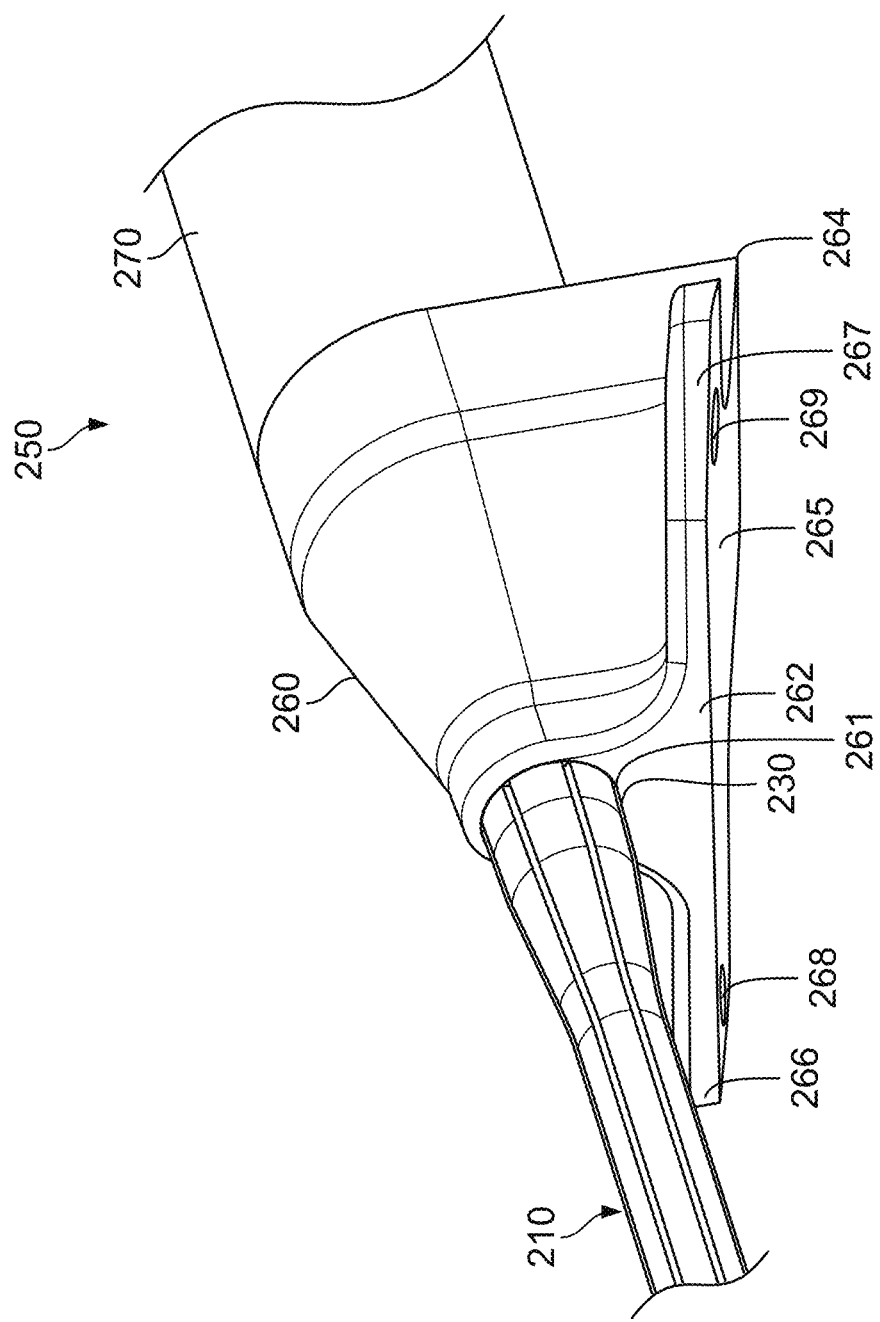
FIG. 9 shows an isometric view of a proximal end of the illustrative expandable sheath of FIG. 2 coupled to a flexible portion of a hub assembly.

FIG. 8 illustrates the proximal end 230 of the sheath body 210 according to certain implementations. The proximal end 230 is flared and has an outer diameter 291 that is larger than the outer diameter 219 of the sheath body 210. The flared proximal end 230 of the sheath body 210 is coupled to the flexible portion 260 of the hub assembly 250 as shown in FIG. 9. The flared proximal end 230 enables the sheath body 210 to be coupled to the hub assembly 250. In other implementations, the flared proximal end 230 of the sheath body 210 is coupled to the rigid portion 270 of the hub assembly 250, with the flexible portion 260 residing around the sheath.

Figure 10A:
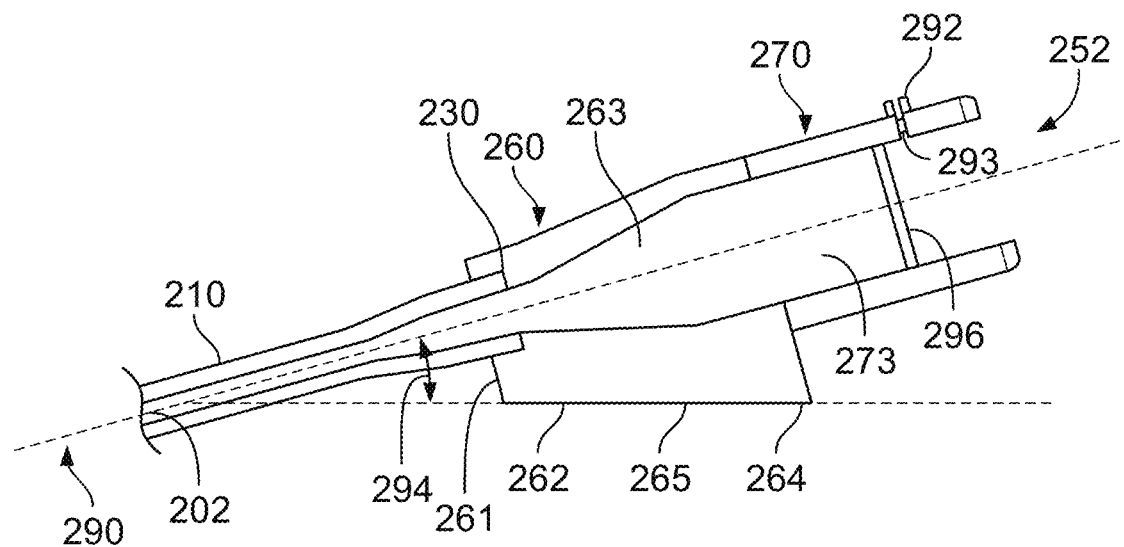
FIG. 10A shows a lateral cross section of an illustrative hub assembly coupled to the proximal end of the illustrative expandable sheath of FIG. 2.
Figure 10B:
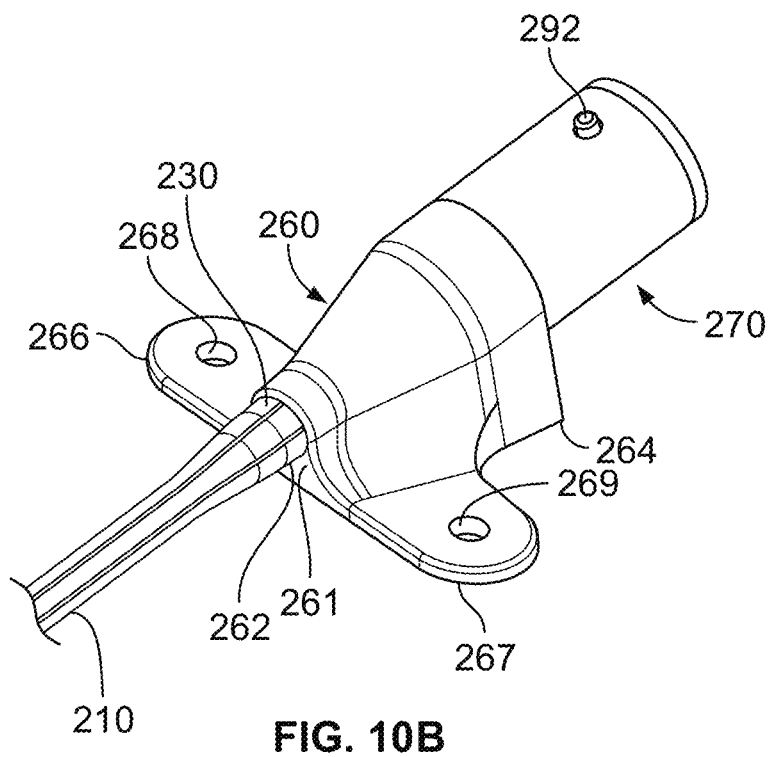
FIG. 10B shows an isometric view of the illustrative hub assembly of FIG. 10A.

FIGS. 9, 10A and 10B show the hub assembly 250 coupled to the proximal end 230 of the sheath body 210. The hub assembly 250 comprises a flexible portion 260 and a rigid portion 270. The hub assembly 250 has an internal conduit 252 that is in fluid communication with the lumen 202 when the hub assembly 250 is coupled to the sheath body 210. The internal conduit 252 of the hub assembly 250 comprises a lumen 263 formed within the flexible portion 260 and a lumen 273 formed within the rigid portion 270. The lumens 263, 273 are in fluid communication with each other. The flexible portion 260 comprises an opening 261, a proximal face 262, a distal face 264, a bottom surface 265, and wings 266, 267. Each of the wings 266, 267 has at least one securing hole 268, 269. The bottom surface 265 is attached to a patient via the securing holes 268, 269 in wings 266, 267. The securing holes 268, 269 may be used to fasten the hub assembly 250 to a patient using sutures. The flexible portion 260 is also designed to be easily attached to a vascular graft with umbilical tape or sutures. This is beneficial during axillary insertions or any other insertions which require pump placement through a vascular graft. In certain implementations, other stabilizations devices, such as surgical tape, a STATLOCK® stabilization device (Bard Access Systems, Inc., Salt Lake City, Utah), or any other suitable adhesive stabilization device may be coupled to the rigid portion 270. The bottom surface 265 is arranged to be angled relative to the sheath body 210. In this configuration, the bottom surface 265 of the flexible portion 260 is at an angle 294 with the longitudinal axis 290 of the sheath body 210. This helps prevent kinking of the sheath body 210 as it orients the axis 290 of the sheath body 210 along a direction of an insertion pathway when the hub assembly 250 is fixated to the patient. While the hub assembly 250 is described as comprising a flexible portion 260 and a rigid portion 270, it will be understood that the hub assembly may comprise a single unit, said unit entirely comprising either a flexible material or a rigid material. In certain implementations, the rigid portion 270 of the hub assembly 250 may be configured with a valve 296 as shown in FIG. 10A, such as a hemostatic valve as described in U.S. patent application Ser. No. 15/245,982 entitled "Hemostatic Valve for Medical Device Introducer," the entire contents of which are hereby incorporated by reference The opening 261 of the flexible portion 260 of the hub assembly 250 is coupled to or engages the flared proximal end 230 of the sheath body 210. Such coupling or engagement may be achieved using any kind of engaging mechanism such as a threaded connection, a press fit connection or a clip-lock connection, for example. As exemplified in FIGS. 9, 10A and 10B, the proximal face 262 of the flexible portion 260 has an external fit with the flared proximal end 230 of the sheath body 210, i.e. the flared proximal end 230 of the sheath body 210 fits within the opening 261 of the flexible portion 260. In this arrangement, the flexible portion 260 of the hub assembly 250 will constrain the proximal end 230 of the sheath body 210 and prevent it from expanding. Once coupled, the sheath body 210 will be in fluid communication with the conduit 252 of the hub assembly 250. In certain implementations, the sheath body 210 may extend through the lumen 263 in the flexible portion 260 and couple to an opening in the rigid portion 270 of the hub assembly 250. In certain implementations, the flexible portion 260 comprises a flexible material. In some implementations, the flexible material is an elastic material with an elastic modulus of about 1.6 ksi. In other implementations, the flexible material is a material with a yield strain of about 200%. In further implementations, the flexible material comprises any one of: ethylene-vinyl acetate (EVA), styrene-butadiene copolymer (SBC) and synthetic rubber. In some implementations, the flexible material comprises an elastomer, such as styrene ethylene butylene styrene (SEBS). The rigid portion 270 comprises a rigid material. In some implementations the rigid material is a polyethylene, polyurethane or polycarbonate material with an elastic modulus of about 40 ksi. In some implementations, the rigid material is any one of a high-density polyethylene (HDPE) material, a medium-density polyethylene (MDPE) material, a low-density polyethylene (LDPE) material, polyether ether ketone (PEEK), and a polyether block amide (such as PEBAX). In certain implementations, the rigid material is a crack-resistant material. In some implementations, the rigid material may also be a material with a low coefficient of friction.

In certain implementations, the rigid portion 270 of the hub assembly 250 has a port 292 that is in fluid communication with the internal conduit 252 of the hub assembly 250. When the sheath body 210 is coupled to the hub assembly 250, the port 282 will therefore also be in fluid communication with the lumen 202 of the sheath body 210. In certain implementations, the port 282 may have a valve 293.

In certain implementations, the port 292 may be used as a flushing port which enables the conduit 252 and the lumen 202 to be flushed with a fluid. When a portion of a medical device is inserted into the expandable sheath 200, hemostasis may develop within the lumen 202 and the conduit 252 in any space between the medical device and the sheath 200. This may result in unwanted clotting if the medical device is contained in the sheath for long periods of time. The port 292 therefore enables the space to be flushed with a fluid. A pressure bag may be connected to the port 292 using any kind of engaging mechanism (e.g. threads, clip lock, etc.). The pressure bag can be used to flush the space between the medical device and the sheath 200 with a fluid to maintain the patency said space thereby preventing any blood clots from forming. Such flushing may be instantaneous or continuous. An infusion pump may be used in combination with the pressure bag to regulate the flow rate of liquid into the patient. For example, the flow rate may be limited to 1 mL/hr, 2 mL/hr, 5 mL/hr, 10 mL/hr, or any other suitable flow rate. The port can also be used to obtain measurement of blood pressure if necessary. In other implementations, the port 292 may be used as a balloon port to inflate balloon.

The expandable sheath 200 is inserted in to the vasculature of a patient using a dilator 1100 as shown in FIG. 11 where the sheath body 210 is assembled with the dilator 1100. The dilator 1100 is inserted into the lumen 202 of the sheath body 210 via the internal conduit 252 of the hub assembly 250. The tapered inner surface 249 of the flexible tip 240 creates a slight inference fit when the dilator 1100 progressed through the tip 240. This creates a smooth or seamless transition from the body of the dilator 110 to the outer surface 206 of the sheath body 210 when the sheath body 210 assembled with the dilator 1100 is inserted into the patient.

Figure 12:
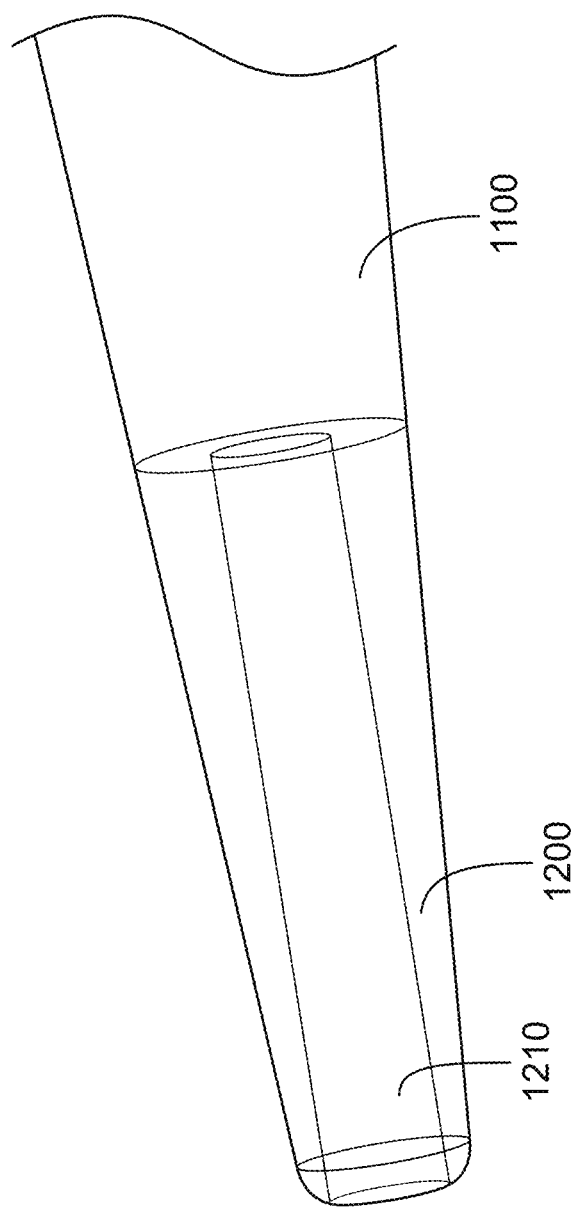
FIG. 12 shows an isometric view of a distal end of a dilator used during insertion of the expandable sheath of FIG. 2.

FIG. 12 illustrates an isometric view of the distal end of the dilator 1100. A fully flexible tip 1200, similar to tip 240, is coupled to the distal end of the dilator 1100. The tip 1200 defines a through hole 1210 for the passage of a guide wire (not shown). The through hole 1210 is connected to a central bore (not shown) within the dilator 1100 through which a guide wire can be threaded. The tip 1200 is configured such that it has a tapered inner wall similar to the inner surface 249 of the tip 240 attached the distal end 220 of the sheath body 210. This creates a slight inference fit when the guide wire is inserted into tip 1200 from the dilator 1100, and provides a seamless transition from the guide wire onto the dilator 1100. The flexibility of the tip 1200 prevents damage of the dilator tip during insertion, improves track-ability of the dilator over the guide wire when maneuvering through an arteriotomy with particularly aggressive insertion angles.

The flexible tip 1200 also prevents vessel puncture, thereby minimizing damage to vessels. In certain implementations the tip 1200 comprises a flexible material. The flexible material is an elastic material with an elastic modulus of about 1.6 ksi. In some implementations, the flexible material is a material with a yield strain of about 200%. In certain implementations, the flexible material comprises any one of: ethylene-vinyl acetate (EVA), styrene-butadiene copolymer (SBC), synthetic rubber, and an elastomer.

Figure 13:
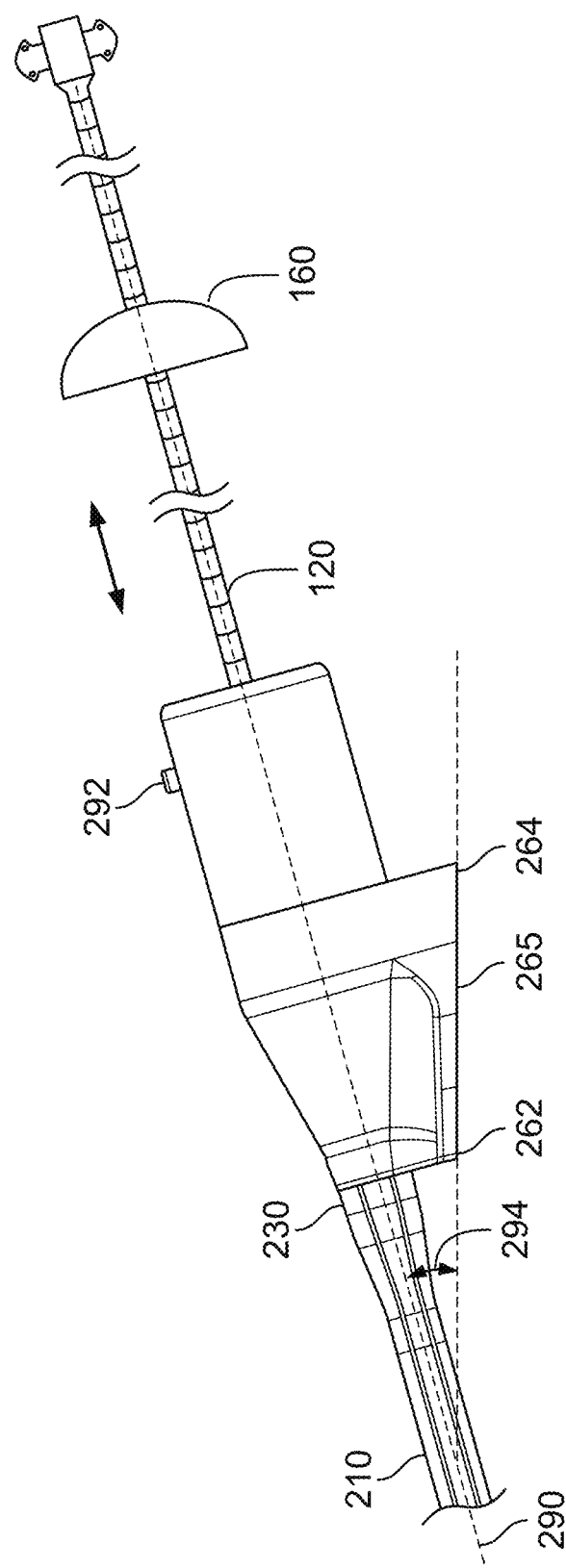
FIG. 13 shows a cross sectional view of the illustrative expandable sheath of FIG. 2 with the hub assembly of FIGS. 9, 10A and 10B coupled to a hub of a medical device inserted into the expandable sheath.

FIG. 13 shows the expandable sheath 200 used in conjunction with a medical device such as the percutaneous heart pump 100 of FIG. 1, after the expandable sheath 200 has been inserted into an insertion site using the dilator 1100, and secured onto the patient via the flexible hub 260 of the hub assembly 250. Once the expandable sheath 200 is in position, the pump head 130 is inserted into the conduit 252 of the hub assembly 250, and into the lumen 202 of the sheath body 210. As the diameter 140 of the pump head 130 is larger than the unexpanded diameter 218 of the lumen 202, the pump head 130 causes the sheath body 210 to expand as it progresses through the lumen 202 from the proximal end 230 to the distal end 220. This expansion is facilitated by the flexible sections 211-217 and rigid sections 281-287 that make up the sheath body 210. When the sheath body 210 expands, the diameter of the lumen 202 increases from 218 to 218', as shown in FIG. 3B. After the pump head 140 has passed through the sheath body 210, the lumen 202 returns to its unexpanded state as depicted in FIG. 3A. The percutaneous pump 100 has a connecting hub 160 fixedly arranged on the catheter body 120. In certain implementations, the connecting hub 160 is used to couple the pump 100 to the hub assembly 250 where hub 160 attaches to the rigid portion 270. Such coupling may be achieved using any kind of engaging mechanism such as a threaded connection, a press fit connection or a clip-lock connection, for example. Such coupling provides a fluid-tight seal between the expandable sheath 200 and the portion of the pump 100 inserted into the sheath 200. The coupling between the hub 160 of the pump 100 and the rigid portion 270 of the hub assembly 200 may also be hemostatic and designed with a sealing feature such as an O-ring or interference fit to prevent blood leaking between the sheath 200 and the catheter body 120. In certain embodiments, once the hub assembly 250 is coupled with the connecting hub 160, fluid can be passed through the port 292 to continuously flush blood out of the space between the expandable sheath body 210 and the pump 100.

Figure 14A:
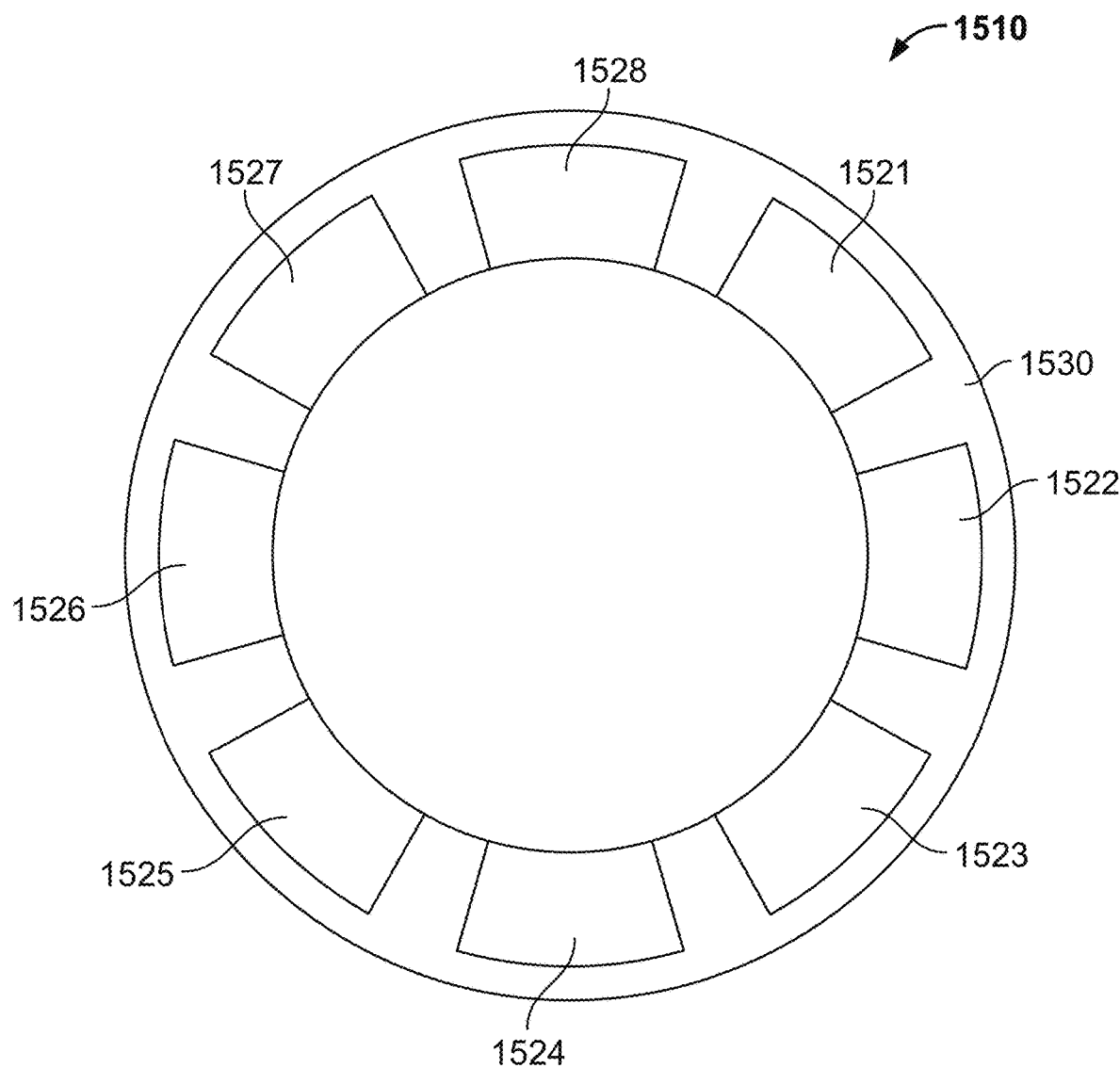
FIGS. 14A to 14C show transverse cross sections of further aspects of the expandable sheath according to the present disclosure.
Figure 14B:
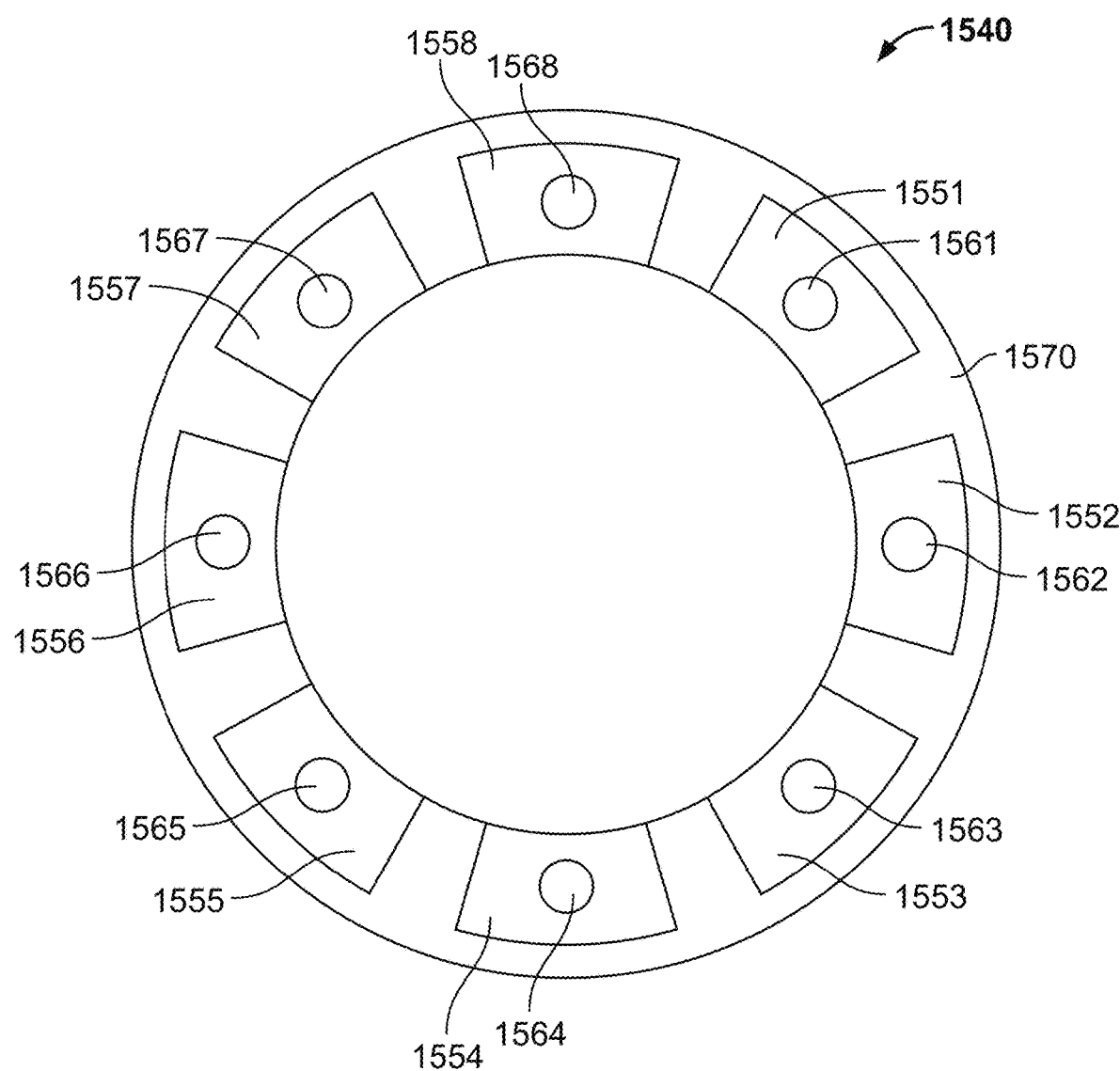
Figure 14C:
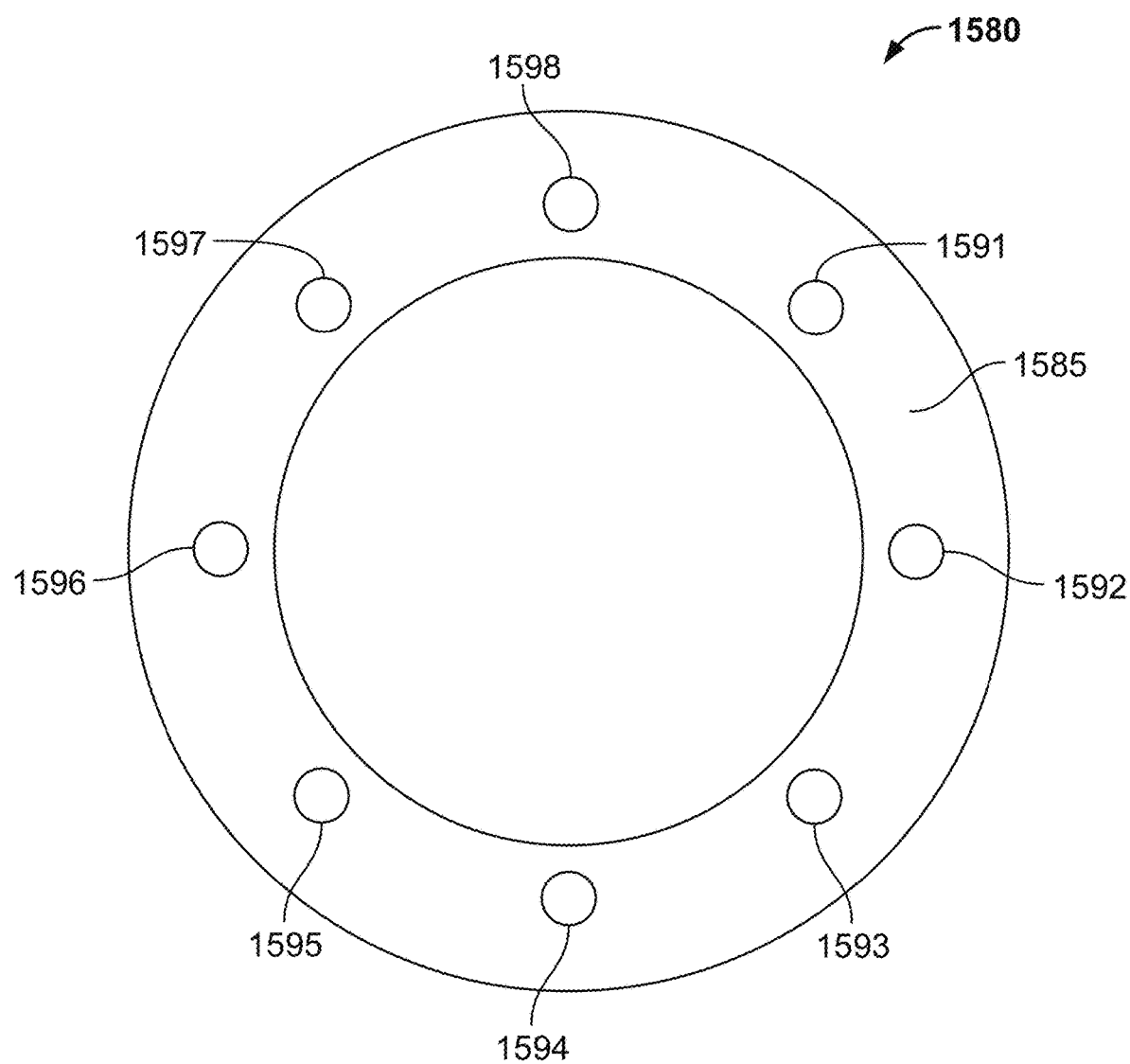

FIGS. 14A-14C illustrate alternative configurations of the expandable sheath 200. FIG. 14A shows a transverse cross-section of the expandable sheath body 1510 according to some implementations. The sheath body 1510 is provided with a plurality of rigid sections 1521-1528 that are partially or fully encapsulated by a flexible material 1530. This configuration of the rigid and flexible sections may be favorable to aid in manufacturability and minimization of stress concentrations at the interface between the rigid sections and flexible section.

FIG. 14B shows a transverse cross-section of the expandable sheath body 1540 according to another implementation. Sheath body 1540 contains a similar cross-section to sheath body 1510, i.e. the sheath body 1540 is provided with a plurality of rigid sections 1551-1558 that are partially or fully encapsulated by a flexible material 1570, with the exception that very rigid sections 1561-1568 have been included in the sheath body 1540. The very rigid sections 1561-1568 comprise a material that is more rigid than the material used for the rigid sections 1551-1558. In some implementations, the material used for the very rigid sections 1561-1568 comprises steel, stainless steel, nitinol (preferred due to its superelasticity), or other metal alloys. The very rigid sections 1561-1568 may comprise a circular cross-section (round wire) or a rectangular cross-section (flat wire). The very rigid sections 1561-1568 further increase the longitudinal stiffness and increases column strength of the sheath body 1540. Each of the very rigid sections 1561-1568 may either be fully encapsulated by the respective rigid sections 1551-1558, or they may be partially encapsulated by the respective rigid sections 1551-1558, depending on the ease of manufacturing. Very rigid sections may also be added to the rigid sections shown in FIGS. 3A-3B and 4A-4C in a manner similar to that illustrated in FIG. 14B.

FIG. 14C shows a transverse cross-section of the expandable sheath body 1580 according to further implementations. The sheath body 1580 comprises very rigid sections 1591-1598 encapsulated by flexible material 1585. Here each of the rigid sections 1591-1598 may either be fully encapsulated by the flexible material 1585, or they may be partially encapsulated by the flexible material 1585, depending on the ease of manufacturing.

The sheath bodies 1510, 1540 and 1580 illustrated in FIGS. 14A-14C adopt similar materials to those used in respect of the sheath body 210 discussed in the preceding sections. Specifically, the flexible material is an elastic material with an elastic modulus of about 1.6 ksi (thousands of pounds per square inch). In some implementations, the flexible material is a material with a yield strain of about 200%. In some implementations, the flexible material contains a radiopaque filler such as bismuth oxychloride or barium sulfate in concentrations of 5% to 40% by weight. In certain implementations, the flexible material comprises any one of: ethylene-vinyl acetate (EVA), styrene-butadiene copolymer (SBC), synthetic rubber, or any other elastomer. The rigid sections comprise a rigid material. The rigid material is a polyethylene or polyurethane material with an elastic modulus of about 40 ksi. In some implementations the rigid material contains a radiopaque filler such as bismuth oxychloride or barium sulfate in concentrations of 5% to 40% by weight. In some implementations, the rigid material is any one of a high-density polyethylene (HDPE) material, a medium-density polyethylene (MDPE) material, a low-density polyethylene (LDPE) material, polyether ether ketone (PEEK), and a polyether block amide (such as PEBAX). In certain implementations, the rigid material is a crack-resistant material. In some implementations, the rigid material may also be a material with a low coefficient of friction.

Figure 15:
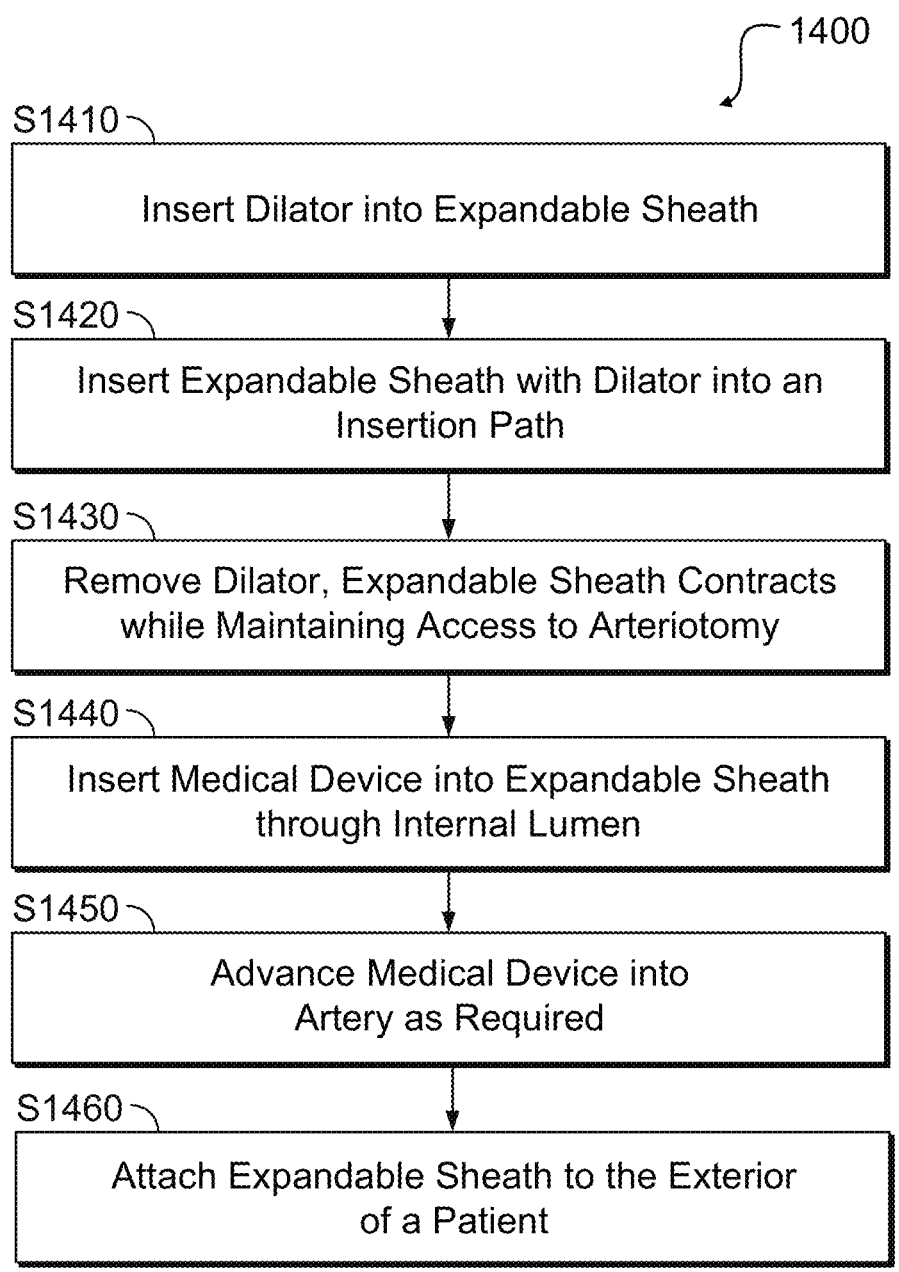
FIG. 15 shows an illustrative method for inserting a medical device into an arteriotomy using the expandable sheath of FIG. 2.

FIG. 15 shows an illustrative method 1400 of using the expandable introducer sheath 200. The illustrative method 1400 may be performed using the expandable introducer sheath 200 or any other suitable sheath tool. At step S1410 a dilator such as dilator 1100 is inserted into the lumen 202 of the sheath body 210 via internal conduit 252 of the hub assembly 250. Once the dilator 1100 is inserted into the sheath body 210, the assembly is inserted into a blood vessel through a percutaneous insertion path as shown in step S1420. The blood vessel may be an artery, such as the femoral artery. The insertion path passes through a blood vessel aperture (e.g., an arteriotomy). When the assembly is in the desired position, the dilator 1100 is removed from the lumen 202 of the sheath body 210 leaving the sheath body 210 in the arteriotomy.

After the dilator 1100 is removed from the sheath body 210, the lumen 202 remains the same diameter in its relaxed date at its smallest internal diameter.

Once the dilator 1100 is removed, a medical device such as a percutaneous pump may be inserted into the lumen 202 of the sheath body 210 via the internal conduit 252 of the hub assembly 250, as shown in step S1440. When the widest portion 130 of the medical device 100 is inserted into the lumen 202 of the sheath 200, the lumen 202 expands and the diameter of the lumen 202 increases from 218 to 218' so as to accommodate the widest portion 130 of the medical device 100, as shown in FIG. 3B. The widest portion 130 of the medical device 100 is then advanced right through the lumen 202 until it exits the distal end 220 of the expandable sheath 200. The medical device 100 is then advanced into the artery of the patient as desired (step S1450).

Once the medical device 100 is in position within the expandable sheath 200, the expandable sheath 200 is then fastened to the patient in step S1460. This may be done via the securing holes 268, 269 in wing 266, 267 of the flexible hub 260. Such fastening may be facilitated with the aid of sutures or medical adhesive tape, for example. Additionally, in certain implementations, the expandable sheath 200 may be fixed in place within the arteriotomy of the patient by inflating a balloon on the outer surface of the sheath body 210.

While the expandable sheath 200 has been described in relation to a percutaneous pump, it can be envisaged that the sheath can be used with a percutaneous pump integrated with a repositioning sheath as described in U.S. Patent Application 62/394,597 entitled "Integrated Expandable Access for Medical Device Introducer," the entire contents of which are hereby incorporated by reference.

In view of the foregoing, the person of ordinary skill will appreciate that the present disclosure provides a means to fixate mechanical devices in place within an expandable sheath, thereby preventing the migration of the device once inserted into the heart. Medical devices of varying diameters may be used with a single expandable sheath.

The foregoing is merely illustrative of the principles of the disclosure, and the systems, methods, and devices can be practiced by other than the described embodiments, which are presented for purposes of illustration and not of limitation. It is to be understood that the systems, methods, and devices disclosed herein, while shown for use in a system percutaneous heart pumps, may be applied to systems, methods, and devices for other implantable heart pumps or implantable cardiac assist devices.

Variations and modifications will occur to those of skill in the art after reviewing the present disclosure. The various features described or illustrated above, including any components thereof, may be combined or integrated in other systems. Moreover, certain features may be omitted or not implemented. The various implementations described or illustrated above may be combined in any manner.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. An expandable sheath comprising:
   a sheath body having an inner surface and an outer surface, the inner surface defining a lumen that extends along a longitudinal axis between a proximal end and a distal end of the sheath body, the sheath body being comprised of:
   a first member extending between the proximal end and the distal end of the sheath body and forming the outer surface of the sheath body, the first member having an inner surface comprising a plurality of cavities extending parallel to the longitudinal axis between the proximal end and the distal end of the sheath body, and the first member comprising a first material having a first elastic modulus;

a plurality of second members, each second member being at least partially encapsulated within a respective cavity of the plurality of cavities of the first member and extending parallel to the longitudinal axis between the proximal end and the distal end of the sheath body, and each second member comprising a second material having a second elastic modulus that is higher than the first elastic modulus; and a plurality of third members, each third member being at least partially encapsulated within a respective second member of the plurality of second members and extending parallel to the longitudinal axis between the proximal end and the distal end of the sheath body, and each third member comprising a third material having a third elastic modulus that is higher than the second elastic modulus, wherein the sheath body is configured to be radially expandable from an unexpanded state to an expanded state to allow passage of a portion of a medical device through the lumen, the portion of the medical device having a transverse cross-sectional area larger than a transverse cross-sectional area of the lumen when the sheath is in the unexpanded state.

2. The expandable sheath of claim 1, wherein the second material comprises at least one of: polyether ether ketone (PEEK), a polyether block amide, a polyethylene material, a high-density polyethylene (HDPE) material, a medium-density polyethylene (MDPE) material, a low-density polyethylene (LDPE) material, or a material with an elastic modulus of about 40 ksi.

3. The expandable sheath of claim 1, wherein the first material comprises at least one of: ethylene-vinyl acetate (EVA), styrene-butadiene copolymer (SBC), synthetic rubber, an elastomer, a material with an elastic modulus of about 1.6 ksi, or a material with a yield strain in excess of 200%.

4. The expandable sheath of claim 1, wherein the sheath body is configured to automatically return to the unexpanded state after passage of the portion of the medical device.

5. The expandable sheath of claim 1, wherein a diameter of the outer surface at the proximal end of the sheath body is larger than a diameter of the outer surface at the distal end of the sheath body, when the sheath body is in the unexpanded state.

6. The expandable sheath of claim 1, wherein the third material comprises at least one of: steel, stainless steel, or nitinol.

7. The expandable sheath of claim 1, further comprising a hub coupled to the proximal end of the sheath body, the hub having at least one hemostatic valve in communication with the lumen of the sheath body.

8. The expandable sheath of claim 1, wherein at least a portion of the inner surface has an irregular geometry comprising at least one of: ribs, projections, or indentations.

9. The expandable sheath of claim 1, wherein the inner surface comprises at least one rib extending between the proximal and distal ends of the sheath body.

10. The expandable sheath of claim 1, further comprising a tapered tip attached to the distal end of the sheath body, the tapered tip comprising an outer surface that is continuous with the outer surface of the sheath body, and which reduces in diameter as it approaches a distal end of the tapered tip.

11. The expandable sheath of claim 10, wherein the tapered tip further comprises an inner surface that is continuous with the inner surface of the sheath body, and which reduces in diameter as it approaches a distal end of the tapered tip.

12. The expandable sheath of claim 11, wherein the inner surface of the tapered tip defines a tip lumen that extends between the distal end of the sheath body and the distal end of the tapered tip, the tip lumen being in fluid communication with the lumen of the sheath body.

13. The expandable sheath of claim 12, wherein the diameter of the inner surface at the distal end of the tapered tip is configured to seal against a second portion of the medical device, the second portion of the medical device having a transverse cross-sectional area smaller than a transverse cross-sectional area of the tip lumen when the sheath body is in the unexpanded state.

14. The expandable sheath of claim 10, wherein the tapered tip comprises at least one of: ethylene-vinyl acetate (EVA), styrene-butadiene copolymer (SBC), synthetic rubber, an elastomer, a material with an elastic modulus of about 1.6 ksi, or a material with a yield strain in excess of 200%.

15. The expandable sheath of claim 10, wherein the tapered tip comprises the first material.

16. The expandable sheath of claim 1, wherein the second elastic modulus is substantially higher than the first elastic modulus.

17. The expandable sheath of claim 10, wherein the outer surface of the tapered tip terminates in a rounded edge at the distal end of the tapered tip.

18. The expandable sheath of claim 1, wherein each second member is fully encapsulated within its respective cavity of the plurality of cavities of the first member.

19. The expandable sheath of claim 1, wherein each third member is fully encapsulated within its respective second member of the plurality of second members.

20. The expandable sheath of claim 18, wherein each third member is fully encapsulated within its respective second member of the plurality of second members.

* * * * *